US008455100B2

(12) United States Patent
Burckhardt

(10) Patent No.: US 8,455,100 B2
(45) Date of Patent: *Jun. 4, 2013

(54) ALDIMINES COMPRISING HYDROXYL GROUPS, AND COMPOSITIONS CONTAINING ALDIMINE

(75) Inventor: Urs Burckhardt, Zurich (CH)

(73) Assignee: Sika Technology AG, Baar (CH)

( * ) Notice: Subject to any disclaimer, the term of this patent is extended or adjusted under 35 U.S.C. 154(b) by 538 days.

This patent is subject to a terminal disclaimer.

(21) Appl. No.: 12/669,717

(22) PCT Filed: Aug. 29, 2008

(86) PCT No.: PCT/EP2008/061400
§ 371 (c)(1),
(2), (4) Date: Jan. 19, 2010

(87) PCT Pub. No.: WO2009/027511
PCT Pub. Date: Mar. 5, 2009

(65) Prior Publication Data
US 2010/0190014 A1    Jul. 29, 2010

(30) Foreign Application Priority Data

Aug. 31, 2007 (EP) .................................... 07115440

(51) Int. Cl.
B32B 27/40 (2006.01)
B32B 9/04 (2006.01)
C07C 251/08 (2006.01)
C07C 249/00 (2006.01)
C08K 5/29 (2006.01)

(52) U.S. Cl.
USPC .................. 428/423.1; 428/425.8; 428/425.9; 564/278; 156/331.7; 524/237

(58) Field of Classification Search
USPC .. 428/423.1, 425.8, 425.9; 564/278; 524/237; 156/331.7
See application file for complete search history.

(56) References Cited

U.S. PATENT DOCUMENTS

| 1,824,676 | A | 9/1931 | Mannich |
| 3,849,156 | A | 11/1974 | Marlin et al. |
| 3,862,879 | A | 1/1975 | Barron et al. |
| 4,224,417 | A | 9/1980 | Hajek et al. |
| 4,515,986 | A | 5/1985 | Bernhagen et al. |
| 4,853,454 | A | 8/1989 | Merger et al. |
| 5,168,110 | A | 12/1992 | Van Den Elshout et al. |
| 5,306,605 | A | 4/1994 | Odenwalder et al. |
| 6,136,942 | A | 10/2000 | Pfenninger et al. |
| 7,597,931 | B2 | 10/2009 | Jones et al. |
| 7,629,433 | B2 | 12/2009 | Burckhardt |
| 8,157,950 | B2 * | 4/2012 | Burckhardt ................ 156/330.9 |
| 2005/0282989 | A1 | 12/2005 | Rosthauser |
| 2006/0149025 | A1 | 7/2006 | Burckhardt |
| 2007/0051832 | A1 | 3/2007 | Jones et al. |
| 2007/0066721 | A1 | 3/2007 | Kramer et al. |
| 2007/0105983 | A1 | 5/2007 | Kramer et al. |
| 2010/0101455 | A1 | 4/2010 | Burckhardt |
| 2010/0190014 | A1 | 7/2010 | Burckhardt |

FOREIGN PATENT DOCUMENTS

| DE | 42 12 795 A1 | 10/1993 |
| DE | 10 2005 042 380 A1 | 3/2007 |
| EP | 0 254 177 A2 | 1/1988 |
| EP | 1 384 709 A1 | 1/2004 |
| EP | 1 772 447 A1 | 4/2007 |
| EP | 1 775 284 A1 | 4/2007 |
| NL | 9000370 A | 9/1991 |
| WO | WO 00/39178 A1 | 7/2000 |
| WO | WO 2004/013088 A1 | 2/2004 |
| WO | WO 2004/055092 A1 | 7/2004 |
| WO | WO 2005/007720 A1 | 1/2005 |
| WO | WO 2007/036571 A1 | 4/2007 |

OTHER PUBLICATIONS

Johnson et al., "The Chemistry of Hindered Systems. Synthesis and Properties of Tetramethylazacycloheptanes and Related Acyclic Amines," J. Org. Chem., vol. 40, No. 19, 1975, pp. 2710-2720.
Methods of Organic Chemistry, Eugen Muller, Editor, 1958, pp. 73-99 (with translation).
International Search Report issued for International Application No. PCT/EP2008/061400 on Jan. 26, 2009 (with translation).
U.S. Appl. No. 12/451,955, filed Dec. 9, 2009, Burckhardt.
Office Action mailed Aug. 4, 2011 issued in U.S. Appl. No. 12/451,955.
"Methoden der organischen Chemie," Houben-Weyl, Methods of Organic Chemistry, vol. X1/2, p. 73-91 (w/translation).
Brown et al., "Modular synthesis of multidentate ligands with variable N-donors: applications to tri- and tetracopper(I) complexes," Dalton Trans., 2007, pp. 3035-3042.
International Search Report issued in International Application No. PCT/EP2008/059267 on Sep. 19, 2008.
International Preliminary Report on Patentability issued for International Application No. PCT/EP2008/061400 on May 4, 2010.
Russian Office Action dated Jun. 9, 2011 issued in Russian Patent Application No. 2010105241 (007394), with English-language translation.

* cited by examiner

Primary Examiner — Thao T. Tran
(74) Attorney, Agent, or Firm — Oliff & Berridge, PLC

(57) ABSTRACT

The present invention relates to aldimines of the formula (I) which have at least one hydroxyl group, and to curable compositions comprising these aldimines. The aldimines can be prepared in a simple manner and are widely usable. The aldehydes formed in the hydrolysis can be incorporated into a polymer via the hydroxyl groups and have tertiary amino groups which can act catalytically.

30 Claims, No Drawings

ALDIMINES COMPRISING HYDROXYL GROUPS, AND COMPOSITIONS CONTAINING ALDIMINE

TECHNICAL FIELD

The invention relates to the field of the aldimines.

STATE OF THE ART

Aldimines are condensation products formed from primary amines and aldehydes, and constitute a substance class which has been known for some time. On contact with water, aldimines can be hydrolyzed to the corresponding amines and aldehydes. Owing to this property, they can be used as a protected form of amines, or of aldehydes. For example, aldimines are used in polyurethane chemistry, where they serve as moisture-activable crosslinkers, known as "blocked amines", or as hardeners, for one or two-component compositions having isocyanate groups.

The use of aldimines as hardeners in compositions having isocyanate groups has some advantages. Firstly, the aldimines have a moderate, efficiently controllable reactivity towards the isocyanate groups, whereas the corresponding free amines react much too quickly and are generally not usable as hardeners. Secondly, the presence of the aldimines prevents the direct carbon dioxide ($CO_2$)-producing reaction of the isocyanate groups with moisture, and hence suppresses the formation of undesired gas bubbles in the composition.

The use of aldimines as hardeners in compositions having isocyanate groups can, however, also cause problems, especially owing to the fact that the curing of such compositions releases aldehydes which are not incorporated into the polymer which forms. Depending on the aldehydes used, the compositions may have a very strong odour which is intolerable for many applications. Moreover, the aldehydes can sweat out of the composition as a result of migration effects or reduce the mechanical strength or durability thereof.

WO 2004/013088 A1 describes odorless polyaldimines which are prepared from primary polyamines and odorless aldehydes. WO 2007/036571 A1 describes odorless aldimines comprising at least one hydroxyl, mercapto or secondary amino group, which are likewise obtainable proceeding from odorless aldehydes. The low volatility of the aldehydes released from these aldimines means that they largely remain in the cured composition, where they may act to cause softening and/or to reduce strength. The relatively high molecular weight of these aldehydes leads, moreover, to a need to use the aldimines in a relatively large amount, which can make them expensive to use.

SUMMARY OF THE INVENTION

It is an object of the present invention to provide novel aldimines which can be used as hardeners in curable compositions, especially in compositions having isocyanate groups with advantageous properties, the aldehydes released being incorporated into the polymer which forms as the compositions are cured.

It has been found that, surprisingly, aldimines according to Claim 1 achieve this object. These are thermally stable, usually room temperature liquid compounds which have barely any odour and are preparable from readily available base materials in a simple process. They have tertiary amino groups of relatively low basicity and can act catalytically in chemical reaction systems. In addition, they bear hydroxyl groups, which are available for further reactions, for example with isocyanate groups.

These aldimines are suitable, for example, as hardeners for curable compositions which contain groups reactive towards amines, such as epoxy groups, anhydride groups and especially isocyanate groups. In compositions having isocyanate groups, the aldehydes released from the aldimines in the course of curing are incorporated covalently into the polyurethane polymer which forms via the hydroxyl groups thereof and thus remain completely in the composition.

The invention further provides aldimines according to Claim 15, which are reaction products of the aldimines according to Claim 1.

The invention further provides curable compositions comprising the aldimines described, according to Claim 17.

Finally, a process for preparing the aldimines according to Claim 12, uses according to Claim 16, and an article according to Claim 29 constitute further subjects of the present invention.

Further aspects of the invention are the subject of further independent claims. Particularly preferred embodiments of the invention are the subject of the dependent claims.

Ways of Performing the Invention

The invention provides aldimines of the formula (I)

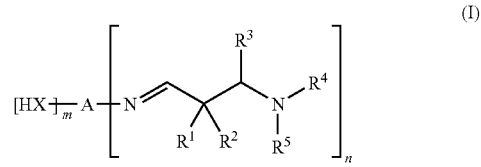

where
A is either
the radical of an amine after removal of n primary aliphatic amino groups and
m HX groups
or together with $R^7$ is an (n+2)-valent hydrocarbon radical which has 3 to 20 carbon atoms and optionally contains at least one heteroatom, especially in the form of ether oxygen or tertiary amine nitrogen;
n is 1 or 2 or 3 or 4;
m is 0 or 1 or 2 or 3 or 4;
$R^1$ and $R^2$ are either
    each independently a monovalent hydrocarbon radical having 1 to 12 carbon atoms
    or together are a divalent hydrocarbon radical having 4 to 12 carbon atoms which is part of an optionally substituted carbocyclic ring having 5 to 8, preferably 6, carbon atoms;
$R^3$ is a hydrogen atom or an alkyl group or an arylalkyl group or an alkoxycarbonyl group, especially having 1 to 12 carbon atoms;
$R^4$ and $R^5$ are either
    each independently a methyl group or a monovalent aliphatic, cycloaliphatic or arylaliphatic radical which has 2 to 12 carbon atoms and optionally has hydroxyl groups and optionally contains heteroatoms in the form of ether oxygen or tertiary amine nitrogen,
    with the proviso that $R^4$ has at least one hydroxyl group,
or
    together are a divalent aliphatic radical which has at least one hydroxyl group and 4 to 12 carbon atoms, and is part of an optionally substituted heterocyclic ring having 5 to 8, preferably 6, ring atoms, this ring optionally containing further heteroatoms in the form of ether oxygen or tertiary amine nitrogen;

X is O or S or N—$R^6$ or N—$R^7$, where $R^6$ is either a monovalent hydrocarbon radical which has 1 to 20 carbon atoms and optionally has at least one carboxylic ester, nitrile, nitro, phosphonic ester, sulphone or sulphonic ester group, or a substituent of the formula (II)

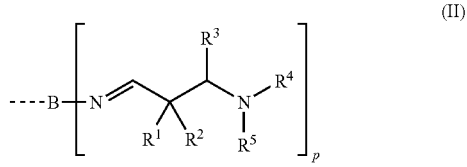

(II)

where p is 0 or an integer from 1 to 10 000, and

B is a (p+1)-valent hydrocarbon radical which optionally contains ether oxygen, tertiary amine nitrogen, hydroxyl groups, secondary amino groups or mercapto groups; and $R^7$ together with A is an (n+2)-valent hydrocarbon radical which has 3 to 20 carbon atoms and optionally contains at least one heteroatom, especially in the form of ether oxygen or tertiary amine nitrogen.

The broken lines in the formulae in this document each represent the bond between a substituent and the rest of the associated molecule.

The term "primary amino group" in the present document denotes an amino group in the form of an $NH_2$ group which is bonded to an organic radical. The term "secondary amino group" denotes an amino group in which the nitrogen atom is bonded to two organic radicals which may also together be part of a ring. The term "tertiary amino group" denotes an amino group in which the nitrogen atom is bonded to three organic radicals, where two of these radicals may also together be part of a ring (=tertiary amine nitrogen).

"Aliphatic" refers to an amine or an amino group in which the nitrogen atom is bonded exclusively to aliphatic, cycloaliphatic or arylaliphatic radicals.

The term "active hydrogen" in the present document refers to the hydrogen atom of a hydroxyl, mercapto or secondary amino group.

$R^1$ and $R^2$ are preferably each a methyl group.

$R^3$ is preferably a hydrogen atom.

$R^4$ and $R^5$ are preferably each a 2-hydroxyethyl group or are each a 2-hydroxypropyl group.

Preferred aldimines of the formula (I) are those in which the $R^4$ and $R^5$ radicals together have at least two hydroxyl groups and the A radical is at least difunctional. Such preferred aldimines of the formula (I) are aldimines of the formula (I')

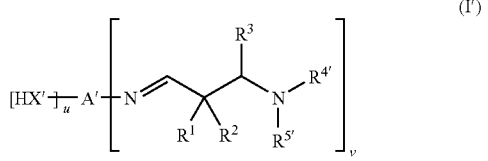

(I')

where

A' is either the radical of an amine after removal of v primary aliphatic amino groups and u HX' groups, or together with $R^{7'}$ is a (v+2)-valent hydrocarbon radical which has 3 to 20 carbon atoms and optionally contains at least one heteroatom, especially in the form of ether oxygen or tertiary amine nitrogen;

u is 1 or 2 or 3 or 4, and v is 0 or 1 or 2 or 3 or 4, with the proviso that u+v is 2 or 3 or 4 or 5;

$R^{4'}$ and $R^{5'}$ are either each independently a methyl group or a monovalent aliphatic, cycloaliphatic or arylaliphatic radical which has 2 to 12 carbon atoms and optionally has hydroxyl groups and optionally contains heteroatoms in the form of ether oxygen or tertiary amine nitrogen, with the proviso that $R^{4'}$ has at least one hydroxyl group, and that $R^{4'}$ and $R^5$ together have at least two hydroxyl groups, or together are a divalent aliphatic radical which has at least two hydroxyl groups and 4 to 12 carbon atoms, and is part of an optionally substituted heterocyclic ring having 5 to 8, preferably 6, ring atoms, this ring optionally containing further heteroatoms in the form of ether oxygen or tertiary amine nitrogen;

X' is O or S or N—$R^{6'}$ or N—$R^{7'}$, where $R^{6'}$ is either a monovalent hydrocarbon radical which has 1 to 20 carbon atoms and optionally has at least one carboxylic ester, nitrile, nitro, phosphonic ester, sulphone or sulphonic ester group, or a substituent of the formula (II')

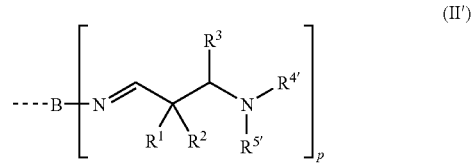

(II')

and $R^{7'}$ together with A' is a (v+2)-valent hydrocarbon radical which has 3 to 20 carbon atoms and optionally contains at least one heteroatom, especially in the form of ether oxygen or tertiary amine nitrogen; and B, p, $R^1$, $R^2$ and $R^3$ are each as already defined.

(u+v) in formula (I') is preferably 2 or 3.

$R^{4'}$ and $R^{5'}$ in formula (I') together preferably have two hydroxyl groups. Such preferred aldimines of the formula (I') contain, in one embodiment, one $R^{4'}$ radical with two hydroxyl groups and one $R^{5'}$ radical with no hydroxyl group; or, in a further embodiment, one $R^{4'}$ radical with one hydroxyl group and one $R^{5'}$ radical with one hydroxyl group.

Particularly preferred aldimines of the formula (I') are, in one embodiment, aldimines of the formula (I a)

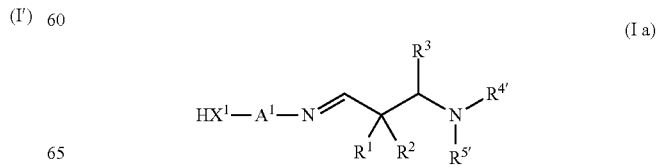

(I a)

where $A^1$ has no active hydrogen and no primary amino groups and is either a divalent hydrocarbon radical which has 2 to 20 carbon atoms and optionally contains at least one heteroatom, especially in the form of ether oxygen or tertiary amine nitrogen, or together with $R^9$ is a trivalent hydrocarbon radical which has 3 to 20 carbon atoms and optionally contains at least one heteroatom, especially in the form of ether oxygen or tertiary amine nitrogen;

$X^1$ is O or S or N—$R^8$ or N—$R^9$, where $R^8$ is either a monovalent hydrocarbon radical which has 1 to 20 carbon atoms and optionally has at least one carboxylic ester, nitrile, nitro, phosphonic ester, sulphone or sulphonic ester group, or a substituent of the formula (II a)

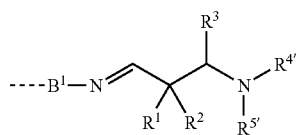

(II a)

where $B^1$ is a divalent hydrocarbon radical which has 2 to 12 carbon atoms and optionally has ether oxygen or tertiary amine nitrogen; and $R^9$ together with $A^1$ is a trivalent hydrocarbon radical which has 3 to 20 carbon atoms and optionally contains at least one heteroatom, especially in the form of ether oxygen or tertiary amine nitrogen;

and $R^1$, $R^2$, $R^3$, $R^{4'}$ and $R^{5'}$ are each as already defined.

Particularly preferred aldimines of the formula (I') are, in a further embodiment, aldimines of the formula (I b)

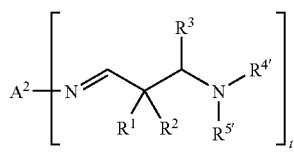

(I b)

where t is 2 or 3;

$A^2$ is the radical of a polyamine with t primary amino groups after removal of t primary amino groups and contains no active hydrogen;

and $R^1$, $R^2$, $R^3$, $R^{4'}$ and $R^{5'}$ are each as already defined.

Aldimines of the formula (I) are obtainable from the reaction of at least one amine B of the formula (III) with at least one sterically hindered, aliphatic aldehyde ALD which has at least one hydroxyl group and is of the formula (IV),

(III)

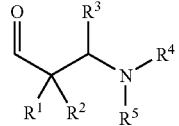

(IV)

where $X^a$ is O or S or N—$R^{6a}$ or N—$R^7$, where $R^{6a}$ is either a monovalent hydrocarbon radical which has 1 to 20 carbon atoms and optionally has at least one carboxylic ester, nitrile, nitro, phosphonic ester, sulphone or sulphonic ester group, or is a substituent of the formula (III')

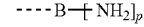

(III')

and m, n, p, A, B, $R^1$, $R^2$, $R^3$, $R^4$ and $R^5$ are each as already defined.

The reaction between an amine B of the formula (III) and an aldehyde ALD of the formula (IV) is effected in a condensation reaction with elimination of water. Such condensation reactions are very well known and are described, for example, in Houben-Weyl, "Methoden der organischen Chemie" [Methods of Organic Chemistry], vol. XI/2, page 73 ff. The aldehyde ALD is used here stoichiometrically or in a stoichiometric excess in relation to the primary amino groups of the amine B. Typically, such condensation reactions are performed in the presence of a solvent, by means of which the water which forms in the reaction is removed azeotropically. To prepare the aldimines of the formula (I), however, preference is given to a preparation process without use of solvents, wherein the water formed in the condensation is removed directly from the reaction mixture by means of application of vacuum. By virtue of the solvent-free preparation, there is no need to distil off the solvent on completion of preparation, which simplifies the preparation process. In addition, the aldimine is thus free of solvent residues which could cause a troublesome odour.

In one embodiment, suitable amines B are primary amines, for example the isomers butyl-, pentyl-, hexyl-, heptyl-, octyl-, nonyl-, decyl-, undecyl-, dodecyl- and tridecylamines, alkoxyalkylamines such as 2-methoxy-ethylamine, 2-ethoxyethylamine, 3-methoxypropylamine, 3-ethoxypropylamine, 3(2-ethylhexyloxy)propylamine and higher homologues, for example 3-(2-meth-oxyethoxy)propylamine, cyclohexylamine, benzylamine and 2-phenylethyl-amine.

Further suitable amines B are compounds which, as well as one or more primary amino groups, have at least one reactive group bearing an active hydrogen in the form of a hydroxyl, mercapto or secondary amino group. Examples of amines B with more than one reactive group bearing an active hydrogen are aliphatic amines bearing more than one secondary amino group and one or more primary amino groups, such as N,N'-bis(3-aminopropyl)ethylenediamine, triethylenetetramine (TETA), tetraethylenepentamine (TEPA), pentaethylenehexamine, and higher homologues of linear polyethyleneimines, N,N'-bis(3-aminopropyl)ethylene-diamine, products from the multiple cyanoethylation or cyanobutylation and subsequent hydrogenation of primary di- and polyamines with a plurality of primary amino groups, such as N,N'-bis(3-aminopropyl)

ethylenediamine, N,N'-bis(3-aminopropyl)-1,4-diaminobutane, N,N'-bis(3-aminopropyl)-2-methyl-1,5-pentanediamine, N,N'-bis(3-amino-1-ethylpropyl)-2-methyl-1,5-pentanediamine, and also polyethyleneimines of different degrees of polymerization (molar mass range 500 to 1 000 000 g/mol), as obtainable, for example, under the Lupasol® trade name from BASF in pure form or as aqueous solutions, these polyethyleneimines comprising, as well as primary and secondary amino groups, also tertiary amino groups;

hydroxylamines bearing more than one hydroxyl group and one or more primary amino groups, especially derivatives of polyalkoxylated trihydric or higher polyhydric alcohols or of polyalkoxylated polyamines, and also amino sugars, for example glucosamine or galactosamine;

hydroxypolyamines bearing at least one hydroxyl group and at least one secondary amino group from the cyanoethylation or cyanobutylation and subsequent hydrogenation of hydroxylamines such as N-hydroxyethyl-1,2-ethanediamine, N-hydroxypropyl-1,2-ethanediamine, N-hydroxyethyl-1,3-propanediamine, N3-hydroxyethyl-1,3-pentanediamine.

Suitable amines B are additionally polyamines which have two or more primary aliphatic amino groups. Examples of amines B having more than three primary aliphatic amino groups are polyvinylamines or copolymers bearing primary amino groups, for example formed from allylamine and (meth)acrylates.

Particularly suitable amines B are firstly amines B1 of the formula (III a)

$$HX^{1a}-A^1-NH_2 \quad \text{(III a)}$$

where
$X^{1a}$ is O or S or N—$R^{8a}$ or N—$R^9$,
where $R^{8a}$ is either a monovalent hydrocarbon radical which has 1 to 20 carbon atoms and optionally has at least one carboxylic ester, nitrile, nitro, phosphonic ester, sulphone or sulphonic ester group,
or a substituent of the formula (III a')

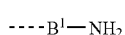

$$----B^1-NH_2 \quad \text{(III a')}$$

and $A^1$, $B^1$ and $R^9$ are each as already defined.

The amines B1 are especially suitable for preparing aldimines of the formula (I a).

Examples of amines B1 are
compounds with one or two primary aliphatic amino groups and one secondary amino group, for example N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethylpiperidine, 3-(4-aminobutyl)piperidine, N-(2-aminoethyl)piperazine, diethylenetriamine (DETA), bishexamethylenetriamine (BHMT), 3-(2-aminoethyl)aminopropylamine; di- and triamines from the cyanoethylation or cyanobutylation and subsequent hydrogenation of primary mono- and diamines, for example N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclo-hexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclohexylamino-1-pentylamine, dipropylenetriamine (DPTA), N3-(3-aminopentyl)-1,3-pentanediamine, N5-(3-aminopropyl)-2-methyl-1,5-pentanediamine, N5-(3-amino-1-ethylpropyl)-2-methyl-1,5-pentanediamine, and fatty diamines such as N-cocoalkyl-1,3-propanediamine, N-oleyl-1,3-propanediamine, N-soyaalkyl-1,3-propanediamine, N-tallowalkyl-1,3-propanediamine or N—($C_{16-22}$-alkyl)-1,3-propanediamine, as obtainable, for example, under the trade name Duomeen® from Akzo Nobel; the products from the Michael-type addition of aliphatic primary di- or triamines with acrylonitrile, maleic or fumaric diesters, citraconic diesters, acrylic and methacrylic esters, acryl- and methacrylamides and itaconic diesters, reacted in a molar ratio of 1:1;

aliphatic hydroxylamines, for example 2-aminoethanol, 2-methylaminoethanol, 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol; derivatives bearing one primary amino group of glycols such as diethylene glycol, dipropylene glycol, dibutylene glycol and higher oligomers and polymers of these glycols, for example 2-(2-aminoethoxy)ethanol, triethylene glycol monoamine, α-(2-hydroxymethylethyl)-ω-(2-aminomethylethoxy)poly(oxy(methyl-1,2-ethanediyl)); derivatives bearing one hydroxyl group and one primary amino group of polyalkoxylated trihydric or higher polyhydric alcohols; products from the single cyanoethylation and subsequent hydrogenation of glycols, for example 3-(2-hydroxyethoxy)propylamine, 3-(2-(2-hydroxyethoxy)ethoxy)propylamine and 3-(6-hydroxyhexyloxy)propylamine;

aliphatic mercaptoamines, for example 2-aminoethanethiol (cysteamine), 3-aminopropanethiol, 4-amino-1-butanethiol, 6-amino-1-hexanethiol, 8-amino-1-octanethiol, 10-amino-1-decanethiol, 12-amino-1-dodecanethiol, and amino thiosugars such as 2-amino-2-deoxy-6-thioglucose.

Preferred amines B1 are N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethylpiperidine, 3-(4-aminobutyl)piperidine, DETA, DPTA, BHMT, and fatty diamines such as N-cocoalkyl-1,3-propanediamine, N-oleyl-1,3-propanediamine, N-soyaalkyl-1,3-propanediamine and N-tallowalkyl-1,3-propanediamine; products from the Michael-type addition reaction of aliphatic primary diamines with maleic and fumaric diesters, acrylic and methacrylic esters, acryl- and methacrylamides, preferably with maleic diesters, especially dimethyl, diethyl, dipropyl and dibutyl maleate, and with acrylic esters, especially methyl acrylate, reacted in a molar ratio of 1:1; and also aliphatic hydroxy- or mercaptoamines in which the primary amino group is separated from the hydroxyl or mercapto group by a chain of at least 5 atoms, or by a ring, especially 5-amino-1-pentanol, 6-amino-1-hexanol and higher homologues thereof, 4-(2-aminoethyl)-2-hydroxyethylbenzene, 3-aminomethyl-3,5,5-trimethylcyclohexanol, 2-(2-aminoethoxy)ethanol, triethylene glycol monoamine and higher oligomers and polymers thereof, 3-(2-hydroxyethoxy)propylamine, 3-(2-(2-hydroxyethoxy)ethoxy)propylamine and 3-(6-hydroxyhexyloxy)propylamine.

Particularly preferred amines B1 are amines which are selected from the group consisting of N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethylpiperidine, 3-(4-aminobutyl)piperidine, DETA, DPTA, BHMT, fatty diamines such as N-cocoalkyl-1,3-propanediamine, N-oleyl-1,3-propanediamine, N-soyaalkyl-1,3-propanediamine and N-tallowalkyl-1,3-propanediamine, 5-amino-1-pentanol, 6-amino-1-hexanol, 4-(2-aminoethyl)-2-hydroxyethylbenzene, 3-aminomethyl-3,5,5-trimethylcyclohexanol, 2-(2-aminoethoxy)ethanol, triethylene glycol monoamine, 3-(2-hydroxyethoxy)propylamine, 3-(2-(2-hydroxyethoxy)ethoxy)propylamine and 3-(6-hydroxyhexyloxy)propylamine.

Particularly suitable amines B are secondly amines B2 of the formula (III b)

where $A^2$ and t are each as already defined.

The amines B2 are especially suitable for preparing aldimines of the formula (I b).

Examples of amines B2 are aliphatic, cycloaliphatic or arylaliphatic diamines, for example ethylenediamine, 1,2-propanediamine, 1,3-propanediamine, 2-methyl-1,2-propanediamine, 2,2-dimethyl-1,3-propanediamine, 1,3-butanediamine, 1,4-butanediamine, 1,3-pentanediamine (DAMP), 1,5-pentanediamine, 1,5-diamino-2-methylpentane (MPMD), 1,6-hexanediamine, 2,5-dimethyl-1,6-hexanediamine, 2,2,4- and 2,4,4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine and methylbis(3-aminopropyl)amine, 1,2-, 1,3- and 1,4-diaminocyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)-methane, bis(4-amino-3-ethyl-5-methylcyclohexyl)methane (M-MECA), 1-amino-3-aminomethyl-3,5,5-trimethylcyclohexane isophoronediamine or IPDA), 2- and 4-methyl-1,3-diaminocyclohexane and mixtures thereof, 1,3- and 1,4-bis(aminomethyl)cyclohexane, 2,5(2,6)bis(aminomethyl)bicyclo-[2.2.1]-heptane (NBDA), 3(4),8(9)bis(aminomethyl)tricyclo[5.2.1.0$^{2,6}$]decane, 1,4-diamino-2,2,6-trimethylcyclohexane (TMCDA), 3,9-bis(3-aminopropyl)-2,4,8,10-tetraoxaspiro[5.5]undecane, and 1,3- and 1,4-xylylenediamine;

aliphatic diamines containing ether groups, for example bis(2-aminoethyl)ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine and higher oligomers of these diamines, bis(3-aminopropyl)polytetrahydrofurans and other polytetrahydrofurandiamines with molecular weights in the range from, for example, 350 to 5200, and polyoxyalkylenediamines. The latter are typically products from the amination of polyoxyalkylenediols and are obtainable, for example, under the Jeffamine® name (from Huntsman Chemicals), under the Polyetheramine name (from BASF) or under the PC Amine® name (from Nitroil). Especially suitable polyoxyalkylenediamines are Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine® ED-2003, Jeffamine® XTJ-568, Jeffamine® XTJ-569, Jeffamine® XTJ-523, Jeffamine® XTJ-536, Jeffamine® XTJ-542, Jeffamine® XTJ-559; Polyetheramine D 230, Polyetheramine D 400 and Polyetheramine D 2000, PC Amine® DA 250, PC Amine® DA 400, PC Amine® DA 650 and PC Amine® DA 2000;

aliphatic triamines such as 4-aminomethyl-1,8-octanediamine, 1,3,5-tris(aminomethyl)benzene, 1,3,5-tris(aminomethyl)cyclohexane;

polyoxyalkylenetriamines, which are typically products from the amination of polyoxyalkylenetriols and are obtainable, for example, under the Jeffamine® trade name (from Huntsman Chemicals), under the Polyetheramine name (from BASF) or under the PC Amine® name (from Nitroil), for example Jeffamine® T-403, Jeffamine® T-5000; Polyetheramine T403, Polyetheramine T5000; and PC Amine® TA 403, PC Amine® TA 5000.

Preferred amines B2 are polyamines which are selected from the group consisting of 1,6-hexamethylenediamine, MPMD, DAMP, IPDA, TMD, 1,3-xylylenediamine, 1,3-bis(aminomethyl)cyclohexane, bis(4-aminocyclo-hexyl)methane, bis(4-amino-3-methylcyclohexyl)methane, 3(4),8(9)-bis(aminomethyl)tricyclo[5.2.1.0$^{2,6}$]decane, 1,2-, 1,3- and 1,4-diaminocyclohexane, 1,4-diamino-2,2,6-trimethylcyclohexane, 3,6-dioxaoctane-1,8-diamine, 4,7-dioxadecane-1,10-diamine, 4-aminomethyl-1,8-octanediamine and polyoxyalkylenepolyamines having two or three amino groups, especially the D-230, D-400, D-2000, T-403 and T-5000 types obtainable under the Jeffamine® trade name from Huntsman, and analogous compounds from BASF or Nitroil.

In the aldehyde ALD of the formula (IV), $R^1$ and $R^2$ are preferably each a methyl group. $R^3$ is preferably a hydrogen atom.

Preferred aldehydes ALD are aldehydes ALD1 which have at least two hydroxyl groups and are of the formula (IV'),

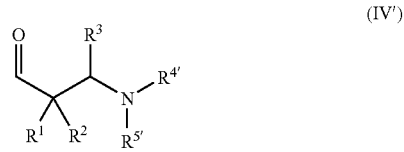

where $R^1$, $R^2$, $R^3$, $R^{4'}$ and $R^{5'}$ are each as already defined.

$R^{4'}$ and $R^{5'}$ in formula (IV') together preferably have two hydroxyl groups.

Aldehydes ALD of the formula (IV) are obtainable especially as the product of a Mannich reaction or of an α-aminoalkylation analogous to the Mannich reaction, as known from the technical literature; they may therefore also be referred to as Mannich bases. An aldehyde Y1 of the formula (V), an aldehyde Y2 of the formula (VI) and a secondary aliphatic amine C which has at least one hydroxyl group and is of the formula (VII) are converted with elimination of water to the aldehyde ALD of the formula (IV),

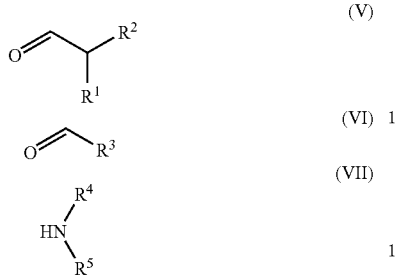

where $R^1$, $R^2$, $R^3$, $R^4$ and $R^5$ are each as already defined.

This reaction can either be conducted with the free reagents Y1, Y2 and C of the formulae (V), (VI) and (VII), or the reagents can be used partly or completely in derivatized form. The aldehyde Y1 can thus be used as the enolate, as the enol ether, especially as the silyl enol ether, or as the enamine. The aldehyde Y2 can be used, for example, in the form of an oligomer—in the case of formaldehyde especially as 1,3,5-trioxane or as paraformaldehyde—or as the hydrate, hemiacetal, acetal, N,O-acetal, animal or hemiaminal. The secondary aliphatic amine C having at least one hydroxyl group, finally, can be used, for example, as the salt, especially as the amine hydrochloride or as the amine hydrosulphate. It is possible to use a portion of the reagents in free form and a portion in derivatized form, or to proceed only from derivatized forms. In the case of use of reagents in derivatized form, the aldehyde ALD is under some circumstances likewise obtained in derivatized form, for example as the salt; in this case, it can be converted by suitable workup to the free form of the formula (IV). According to the circumstances, it may be advisable additionally to use assistants such as Lewis acids or catalysts in such conversion reactions.

In addition, the reaction can be conducted as a one-pot reaction in which all three reagents can react simultaneously with one another; or else a stepwise method can be selected, by first reacting two of the reagents with one another and then reacting the intermediate thus obtained with the third reagent, it being possible to isolate the intermediate or not. Suitable intermediates of this kind are especially iminium salts, which are obtained from the reaction of an aldehyde Y2, in free or derivatized form, with a salt of a secondary aliphatic amine C having at least one hydroxyl group, and which can be reacted with an aldehyde Y1, in free or derivatized form, to give the corresponding salt of an aldehyde ALD of the formula (IV). Such a stepwise method may have the advantage of enabling milder reaction conditions and hence of providing a higher product yield.

In addition, the reaction can be performed using solvents, especially polar solvents such as water or alcohols, or the reaction can be effected without use of solvents.

In a preferred embodiment, the reaction is conducted as a one-pot reaction with all reagents in free form and the aldehyde ALD is purified by distillation on completion of reaction. Preference is given to using no organic solvents.

Examples of suitable aldehydes Y1 of the formula (V) are the following aldehydes: isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde and diphenylacetaldehyde. Preference is given to isobutyraldehyde.

Examples of suitable aldehydes Y2 of the formula (VI) are the following aldehydes: formaldehyde, acetaldehyde, propionaldehyde, butyraldehyde, isobutyraldehyde, phenylacetaldehyde, benzaldehyde and substituted benzaldehydes, and also glyoxylic esters, especially ethyl glyoxylate. Preference is given to formaldehyde.

Suitable amines C of the formula (IV) are secondary aliphatic amines which have a hydroxyl group, for example those which are selected from the group consisting of alkoxylates of primary amines, such as 2-(N-methylamino)ethanol, 2-(N-ethylamino)ethanol, 2-(N-propylamino)ethanol, 2-(N-isopropylamino)ethanol, 2-(N-butylamino)ethanol, 2-(N-cyclo-hexylamino)ethanol, 3-(N-methylamino)-2-propanol, 3-(N-ethylamino)-2-propanol, 3-(N-propylamino)-2-propanol, 3-(N-isopropylamino)-2-propanol, 3-(N-butylamino)-2-propanol, 3-(N-cyclohexylamino)-2-propanol, 2-(N-ethylaminoethoxy)ethanol; cycloaliphatic hydroxylamines such as 2-pyrrolidino-methanol, 3-hydroxypyrrolidine, 2-piperidinemethanol, 3- or 4-hydroxypiperidine and 1-(2-hydroxyethyl)piperazine.

Particularly suitable amines C of the formula (IV) are secondary aliphatic amines C1 which have at least two hydroxyl groups. The amines C1 are especially suitable for preparing the preferred aldehydes ALD1 of the formula (IV').

Suitable amines C1 having two hydroxyl groups are especially selected from the group consisting of diethanolamine, dipropanolamine, diisopropanolamine, 3-(2-hydroxyethylamino)-1-propanol and 3-(2-hydroxypropylamino)-1-propanol, N-methyl-2,3-dihydroxypropylamine, 3,4-dihydroxypyrrolidine, 2,5-bis(hydroxymethyl)pyrrolidine, 2,6-bis(hydroxymethyl)piperidine, 3,4- or 3,5-dihydroxypiperidine, 2-(2,3-dihydroxypropyl)pyrrolidine and 2-(2,3-dihydroxypropyl)piperidine, and the reaction products of ammonia with two molecules which each have an epoxy group, especially a glycidyl ether group.

Suitable amines C1 having more than two hydroxyl groups are, for example, as follows: 2-(2,3-dihydroxypropylamino) ethanol, 3,4,5-trihydroxy-piperidine, N,N-bis(2,3-dihydroxypropyl)amine, 2,5-bis(2,3-dihydroxypropyl)-pyrrolidine and 2,6-bis(2,3-dihydroxypropyl)piperidine.

Preferred amines C1 are diethanolamine and diisopropanolamine.

Preferred aldehydes ALD1 of the formula (IV') are 3-(N-bis(2-hydroxy-ethyl)amino)-2,2-dimethylpropanal and 3-(N-bis(2-hydroxy-2-methylethyl)-amino)-2,2-dimethylpropanal.

The aldehydes ALD of the formula (IV) have a series of special properties. For instance, they possess a good thermal stability because the carbon atom in the α position to the aldehyde group does not bear a hydrogen atom, and the elimination of a secondary amine to form an alkene is therefore impossible. They also have a surprisingly good stability with respect to oxidation by atmospheric oxygen. Moreover, the basicity thereof is surprisingly significantly lower than expected for aliphatic amines of similar structure; the $pK_a$ measured for the conjugated acid of an aldehyde ALD is about 2 units lower than that of the conjugated acid of the secondary amine C used to prepare this aldehyde ALD. These surprising properties are possibly connected to an intramolecular 1,4 interaction between amine group and aldehyde group (orbital overlap between the free electron pair of the nitrogen and the π or π* orbital of the carbonyl), as postulated by P. Y. Johnson et al. (J. Org. Chem., vol. 40, no. 19, 1975; pages 2710-2720) on the basis of NMR and UV spectroscopy studies on β-aminoaldehydes.

Finally, the aldehydes ALD, even in the case of relatively low molecular weight, have only an extremely slight odour, if any. This property of low odour intensity, which is surprising for aldehydes, results firstly from the fact that the aldehydes ALD are not very volatile owing to the OH groups present. Moreover, the low odour is probably promoted by the intramolecular 1,4 interaction mentioned and by the steric hindrance of the aldehyde group which is on a tertiary carbon atom.

The hydroxyl groups of the aldehydes ALD enable further reactions to form further-functionalized reaction products. The preferred aldehydes ALD1 of the formula (IV') which have at least two hydroxyl groups can be used especially as hardeners for compositions which contain components reactive towards hydroxyl groups, for example isocyanate groups.

Aldimines of the formula (I) can, as already described, be prepared directly from amines B and aldehydes ALD.

Aldimines of the formula (I) which have an N—R⁶ substituent as the substituent X can optionally be prepared by a slightly different route than that described so far. This synthesis route consists in reacting an aldehyde ALD of the formula (IV) with a di- or trifunctional, preferably difunctional, aliphatic primary amine, as already described previously as amine B2, in a first step to give an intermediate which, as well as one or two aldimino groups, also contains one or two primary amino groups, preferably one primary amino group. This intermediate is subsequently converted in a second step to an aldimine of the formula (I), by monoalkylating the primary amino group. The compounds used for the alkylation are especially those with only one activated double bond which can enter into Michael-type addition reactions with primary amines; such compounds are referred to hereinafter as "Michael acceptors".

An aldehyde ALD is reacted with an amine B2 to give the intermediate having a primary amino group in a condensation reaction with elimination of water, as described further above for the reaction of an aldehyde ALD with an amine B of the formula (III). However, the stoichiometry between the aldehyde ALD and the amine B2 is selected such that 1 mol of aldehyde ALD is used for 1 mol of amine B2, which contains two primary amino groups, or in such a way that 2 mol of aldehyde ALD are used for 1 mol of amine B2 which contains three primary amino groups. The amine B2 used is preferably asymmetric in relation to the amino groups. Preference is given to a solvent-free preparation process wherein the water formed in the condensation is removed from the reaction mixture by means of application of vacuum.

The intermediate having one primary amino group is reacted with the Michael acceptor, for example, by mixing the intermediate with a stoichiometric or slightly superstoichiometric amount of the Michael acceptor and heating the mixture at temperatures of 20 to 110° C. until complete conversion of the intermediate to the aldimine of the formula (I). The reaction is effected preferably without the use of solvents.

Preferred amines B2 for this preparation are diamines in which the primary amino groups are separated by a chain of at least five atoms, or by a ring, especially 1,5-diamino-2-methylpentane, 1,6-hexamethylenediamine, 2,2,4- and 2,4,4-trimethylhexamethylenediamine and mixtures thereof, 1,10-decanediamine, 1,12-dodecanediamine, 1,3- and 1,4-diaminocyclohexane, bis(4-aminocyclohexyl)methane, bis(4-amino-3-methylcyclohexyl)methane, 1-amino-3-aminomethyl-3,5,5-trimethylcyclohexane, 1,3- and 1,4-bis(aminomethyl)cyclohexane, 2,5(2,6)bis(aminomethyl) bicyclo[2.2.1]heptane, 3(4),8(9)bis(aminomethyl)tricyclo[5.2.1.0²,⁶]decane, 1,4-diamino-2,2,6-trimethylcyclohexane (TMCDA), 3,9-bis(3-aminopropyl)-2,4,8,10-tetraoxaspiro[5.5]undecane, 1,3- and 1,4-xylylenediamine, and also the aliphatic diamines containing ether groups and polyoxyalkylenediamines mentioned.

Examples of suitable Michael acceptors are maleic or fumaric diesters such as dimethyl maleate, diethyl maleate, dibutyl maleate, diethyl fumarate; citraconic diesters such as dimethyl citraconate; acrylic or methacrylic esters such as methyl (meth)acrylate, ethyl (meth)acrylate, butyl (meth)acrylate, lauryl (meth)acrylate, stearyl (meth)acrylate, tetrahydrofuryl (meth)acrylate, isobornyl (meth)acrylate; itaconic diesters such as dimethyl itaconate; cinnamic esters such as methyl cinnamate; vinylphosphonic diesters such as dimethyl vinylphosphonate; vinylsulphonic esters, especially aryl vinylsulfonate; vinyl sulphones; vinyl nitriles such as acrylonitrile, 2-pentenenitrile or fumaronitrile; 1-nitroethylenes such as β-nitrostyrene; and Knoevenagel condensation products, for example those formed from malonic diesters and aldehydes such as formaldehyde, acetaldehyde or benzaldehyde. Preference is given to maleic diesters, acrylic esters, phosphoric diesters and vinyl nitrites.

Those embodiments of aldimines of the formula (I) which have at least one HX group may be in equilibrium with cyclic forms, as shown in formula (VIII) by way of example for the case where the index m=1. These cyclic forms are cyclic aminals, for example imidazolidines or tetrahydropyrimidines, in the case of aminoaldimines, cyclic amino acetals, for example oxazolidines or tetrahydrooxazines, in the case of hydroxyaldimines; cyclic thioaminals, for example thiazolidines or tetrahydrothiazines, in the case of mercaptoaldimines.

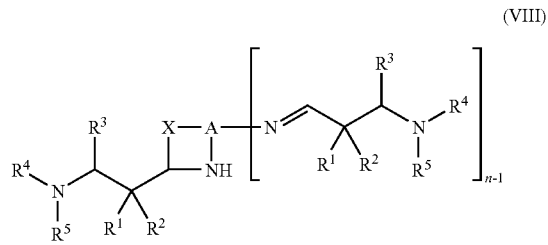

(VIII)

In the formula (VIII), n, A, X, R¹, R², R³, R⁴ and R⁵ are each as already defined.

Surprisingly, most aldimines of the formula (I) containing HX groups do not tend to cyclize. Especially for amino aldimines, it is possible to show by means of IR and NMR spectroscopy methods that these compounds are present predominantly in the open-chain form, i.e. the aldimine form, whereas the cyclic form, i.e. the aminal form, occurs only in traces, if at all. Hydroxy- and mercaptoamines in which the primary amino group is separated from the hydroxyl group or the mercapto group by a chain of at least 5 atoms, or by a ring, exhibit barely any cyclization.

The aldimines of the formula (I) are novel compounds which have not been described to date and have surprising properties. They contain sterically hindered aldimino groups which do not have a hydrogen atom on the carbon atom in the α position and therefore cannot tautomerize to enamino groups. As a result, these aldimino groups are particularly well-protected ("blocked") primary amino groups which, in the presence of water, exhibit moderate, efficiently controllable reactivity with groups reactive towards amines, such as epoxy groups, anhydride groups and especially isocyanate groups, which is in stark contrast to the high reactivity of the corresponding free amino groups from which the aldimino groups are derived. Moreover, the aldimines of the formula (I) have a tertiary amino group which can display catalytic action in chemical reaction systems under some circumstances; the basicity of the aldimines of the formula (I) originating from the tertiary amino group is, however, as already described for the aldehydes ALD of the formula (IV), relatively low. Moreover, the aldimines of the formula (I), even at relatively low molecular weight of the parent aldehyde ALD, have only a slight, amine-like odour, if any.

The aldimines of the formula (I) possess good thermal stability, since the carbon atom in the α position to the aldimino group, as mentioned, does not bear a hydrogen atom and the elimination of a secondary amine to form an alkene is therefore impossible.

The aldimines of the formula (I) are storage-stable under suitable conditions. On ingress of moisture, the aldimino groups thereof can be hydrolyzed in a formal sense via intermediates to amino groups, which releases the corresponding aldehydes ALD of the formula (IV) used to prepare the aldimines, which, as already described, are low-odour or odorless. Since this hydrolysis reaction is reversible and the chemical equilibrium is clearly to the aldimine side, it can be assumed that, in the absence of compounds reactive towards amines, only some of the aldimino groups hydrolyze partly or completely. Surprisingly, the hydrolysis of the aldimino groups, in spite of the presence of tertiary amino groups, can be catalyzed by means of acids.

The aldimines of the formula (I) have at least one hydroxyl group on the aldehyde moiety. As a result, further reactions of these hydroxyl groups with compounds reactive towards hydroxyl groups are possible, especially also on completion of release of the aldehyde ALD in the course of hydrolysis of the aldimino groups.

The aldimines of the formula (I) are preparable in a relatively simple process from readily available starting substances. If nonviscous amines B of the formula (III) were used in the preparation thereof, some of the corresponding aldimines of the formula (I) are likewise nonviscous compounds.

The aldimines of the formula (I) can be used very widely. They can be used, for example, wherever they can serve as a source of aldehydes ALD of the formula (IV) or of amines B of the formula (III). More particularly, they can be used in the function of protected amines, or protected aldehydes, in aldehyde- and/or amine-reactive systems and be deprotected there selectively if required. More particularly, they find use in systems in which compounds which react with primary amines and/or with hydroxyl groups are present. The deprotection of the primary amino groups is effected hydrolytically, for example by contact with water or moisture, especially air humidity. Surprisingly, the hydrolysis of the aldimino groups, in spite of the presence of tertiary amino groups, can be catalyzed by means of acids in the same way as for aldimines without tertiary amino groups in the molecule.

On the other hand, aldimines of the formula (I) with the index m greater than zero find use in the formation of further-functionalized reaction products of these aldimines. For instance, aldimines of the formula (I) with the index m greater than zero can be reacted with compounds which can react with the HX group, especially when the HX groups are secondary amino groups. Compounds suitable for reaction with the HX group bear reactive groups, for example isocyanate groups, epoxy groups, anhydride groups or more or less highly activated double or triple bonds such as (meth)acrylate groups, acrylamide groups, 1-ethynylcarbonyl groups, 1-propynylcarbonyl groups, maleimide groups, citraconimide groups, vinyl groups, isopropenyl groups or allyl groups. The reaction products bearing aldimino groups from such addition reactions can be hydrolyzed if required to aldehydes ALD of the formula (IV) and compounds with primary amino groups, and then be utilized for further reactions, for example for crosslinking reactions, the hydrolysis reaction being catalyzable by means of acids.

Moreover, the aldimines of the formula (I) can be used as catalysts in chemical reaction systems, for example in curable compositions having isocyanate groups, especially in order to shorten the curing time thereof.

Finally, the aldimines of the formula (I) can be used as a source of cationic compounds, by protonating some or all of the tertiary amino groups to ammonium groups or alkylating some or all to quaternary ammonium groups. By protonating or alkylating aldimines of the formula (I), aldimines of the formula (IX) are obtainable

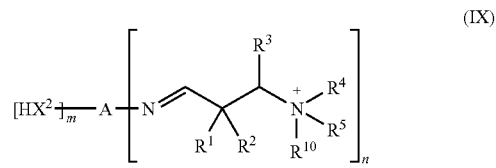

(IX)

where
$R^{10}$ is a hydrogen atom or an alkyl, cycloalkyl or arylalkyl radical having 1 to 20 carbon atoms;
$X^2$ is O or S or N—$R^{11}$ or N—$R^7$;
  where $R^{11}$
  is either a monovalent hydrocarbon radical which has 1 to 20 carbon atoms and optionally has at least one carboxylic ester, nitrile, nitro, phosphonic ester, sulphone or sulphonic ester group,
  or is a substituent of the formula (IX')

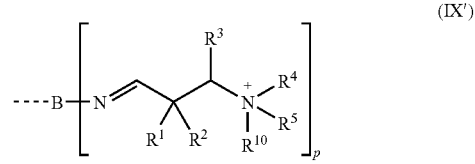

(IX')

and m, n, p, A, B, $R^1$, $R^2$, $R^3$, $R^4$, $R^5$ and $R^7$ are each as already defined.

Aldimines of the formula (IX) are additionally obtainable proceeding from one of the amines B of the formula (III) mentioned above and an aldehyde ALD of the formula (IV), some or all of the tertiary amino groups of the aldehyde ALD being protonated or alkylated before the reaction with the amine B.

To protonate the aldimines of the formula (I) or the aldehydes ALD, it is possible to use any desired Brønsted acids, for example hydrochloric acid, sulphuric acid, phosphoric acid, carboxylic acids such as acetic acid or benzoic acid, and sulphonic acids such as methanesulphonic acid or p-toluenesulphonic acid. To alkylate the aldimines of the formula (I) or the aldehydes ALD, it is possible to use known alkylating agents, especially methylating agents, for example methyl iodide, dimethyl sulphate, dimethyl phosphonate, diazomethane, methyl fluorosulphate or trimethyloxonium tetrafluoroborate.

It is clear to the person skilled in the art that a cationic aldimine of the formula (IX) also includes an anion which balances the positive charge of the aldimine.

The aldimines of the formula (I) or of the formula (IX), especially the preferred aldimines of the formula (I') which have at least two hydroxyl groups, are particularly suitable for use as a constituent of compositions based on isocyanates or epoxy resins, especially for applications such as adhesives, sealants, potting compositions, coatings, floor coverings, paints, coating materials, primers and foams. Such compositions preferably comprise at least one acid, especially an organic carboxylic or sulphonic acid, or a compound hydrolyzable to these acids, the acid surprisingly catalysing the hydrolysis of the aldimino groups in spite of the presence of tertiary amino groups.

More particularly, the aldimines of the formula (I) or the aldimines of the formula (IX), especially the aldimines of the formula (I') which have at least two hydroxyl groups, are suitable as hardeners or as precursors for hardeners for one- or two-component compositions having isocyanate groups, such as adhesives, sealants, potting compositions, coatings, floor coverings, paints, coating materials, primers and foams. The aldehydes ALD of the formula (IV) released in the course of hydrolysis of the aidimino groups react via their hydroxyl groups with the isocyanate groups, and are thus incorporated covalently into the polymer which forms in the course of curing. In the case of use of aldimines of the formula (I'), aldehydes ALD1 which bear at least two hydroxyl groups are released; these may in turn serve as hardeners, by contributing to the chain extension and/or crosslinking of the polymer which forms and not leading to chain terminations.

As already mentioned, the aldimines of the formula (I) contain sterically hindered aldimino groups which are not tautomerizable to enamino groups and are particularly well-protected ("blocked") primary amino groups. These react in the presence of water with isocyanate groups present, the reactivity of which is greatly reduced compared to the corresponding free primary amino groups, such that such systems have an efficiently controllable curing rate.

The hydroxyl groups of the aldehydes ALD released likewise react with isocyanate groups present and are thus, as mentioned, incorporated covalently into the polymer which forms in the course of curing, which is very advantageous. As a result of the incorporation of the aldehydes, they do not cause any adverse effects in the composition, for example increased shrinkage, emissions into the ambient air, especially of unpleasant odours, or migration effects such as sweating; they likewise do not have an adverse effect on the mechanical properties of the composition, for example by having a plasticizing effect or reducing the stability of the composition with respect to environmental influences such as heat or UV radiation. As already mentioned, aldimines of the formula (I') are preferred, since the aldehydes ALD1 released therefrom bear at least two hydroxyl groups, and are thus incorporated covalently into the polymer which forms as at least difunctional hardeners with chain extension or crosslinking in the course of curing of compositions having isocyanate groups.

In compositions having isocyanate groups and comprising aldimines of the formula (I) or of the formula (IX) as hardeners, the hydroxyl groups and any secondary amino groups present react directly with the isocyanate groups, while the aldimino groups react with the isocyanate groups in the presence of water with hydrolysis. The isocyanate groups react with the primary amino groups which are released in a formal sense by the hydrolysis of the aldimino groups, which releases the corresponding aldehyde ALD in free or already adducted form. Excess isocyanate groups relative to the aldimino groups, secondary amino groups and hydroxyl groups react directly with moisture to form urea groups. In the case of suitable stoichiometry between isocyanate groups and the aldimines of the formula (I), the composition cures as a result of these reactions; this process is also referred to as crosslinking. The reaction of the isocyanate groups with the aldimino groups being hydrolyzed need not necessarily proceed via free amino groups. It will be appreciated that reactions with intermediates of the hydrolysis reaction are also possible. For example, it is conceivable that an aldimino group being hydrolyzed reacts directly with an isocyanate group in the form of a hemiaminal. It is also irrelevant for the curing of such a composition whether the hydroxyl groups in the aldehyde moiety of the aldimines react with isocyanate groups before the aldimino groups are hydrolyzed, or only thereafter. As soon as sufficient moisture is present in the composition, for example from air in the form of air humidity, the hydrolysis of the aldimino groups and reaction of the primary amino groups released in a formal sense with isocyanate groups takes place, even if the hydroxyl groups present have already reacted with isocyanate groups. Surprisingly, the acid-catalyzed hydrolysis of the aldimino groups is not impaired by the presence of tertiary amino groups.

The tertiary amino group of the aldimines of the formula (I) may have a catalytic effect on the reaction of the isocyanate groups and may therefore accelerate the crosslinking. This accelerating action is additionally promoted by the fact that the tertiary amino groups are localized in the aldehyde moiety of the aldimines. It is, however, advantageous that the basicity of the tertiary amino groups is comparatively low, since strongly basic tertiary amines can excessively accelerate the direct reaction of the isocyanate groups, especially with water, which can have a disruptive effect in the curing. The hydrolysis of the aldimino groups releases aldehydes ALD of the formula (IV) containing the tertiary amino group and at least one hydroxyl group. The aldehydes ALD are incorporated covalently into the polymer which forms via the reaction of the hydroxyl groups with isocyanate groups. After the incorporation into the polymer, the catalytic activity of the tertiary amino group is significantly reduced owing to its restricted mobility, which may be advantageous for the stability of the material. The aldehyde groups formed in the course of hydrolysis of the aldimino groups are conserved in the course of curing, and can, if desired, be used for further reactions.

It is also possible to store the aldimines of the formula (I) together with water. Only when the water-aldimine mixture comes into contact with isocyanate groups does the hydrolysis proceed to completion. This is because the reaction between aldimines of the formula (I) and isocyanate groups is highly retarded compared to the reaction of the corresponding free amines even when the aldimines were stored together with water or water is present in excess.

It is likewise possible to use aldimines of the formula (I) or of the formula (IX) in compositions which cure under the influence of heat, for example by the use of compounds with thermally labile, blocked isocyanate groups. It is additionally possible to use aldimines of the formula (I) or of the formula (IX) in compositions which constitute reactive warm- or hot-melt adhesives. Such adhesives comprise meltable compounds especially having isocyanate groups; they are solid at room temperature and are applied warm or hot.

The invention further provides curable compositions comprising at least one polyisocyanate and at least one aldimine of the formula (I) or of the formula (IX).

The term "polyisocyanate" in the present document encompasses compounds having two or more isocyanate groups, irrespective of whether they are monomeric diisocyanates, oligomeric polyisocyanates or polymers which have isocyanate groups and have a relatively high molecular weight.

Suitable aldimines of the formula (I) are the aldimines of the formula (I) described in detail above, or the preferred embodiments thereof, especially the aldimines of the formula (I'). Suitable aldimines of the formula (IX) have already been described above.

Preference is given to curable compositions comprising at least one polyisocyanate and at least one aldimine of the formula (I'), especially at least one aldimine of the formula (I a) or of the formula (I b).

In one embodiment, the curable composition has one component.

In the present document, a "one-component" composition refers to a curable composition in which all constituents of the composition are stored mixed in the same container, and which is storage-stable over a prolonged period at room temperature, i.e. the performance or use properties thereof change only insignificantly, if at all, as a result of the storage, and which cures through the action of moisture and/or heat after application.

The one-component curable composition especially comprises at least one polyisocyanate whose isocyanate groups are especially present in the form of blocked isocyanate groups.

A "blocked isocyanate group" in the present document is understood to mean an isocyanate group whose reactivity towards nucleophiles, as a result of the above reaction of a free isocyanate group with a blocking agent known from the prior art, for example a phenol, a ketoxime, a pyrazole, a lactam, or a malonic diester, has been reduced to such a degree that it is storage-stable together with suitable hardeners at room temperature and only begins to react with these hardeners under the action of heat and/or moisture, the blocking agent being released or not being released according to the type.

Suitable polyisocyanates with blocked isocyanate groups are commercially available, for example under the trade names Desmocap® 11, 12 and XP 2540 (all from Bayer), Trixene® BI 7641, BI 7642, BI 7770, BI 7771, BI 7772, BI 7774 and BI 7779 (all from Baxenden), Vestanat® B 1358A, B 1358/100 or B 1370 (all from Degussa), and Tolonate® D2 (from Rhodia), or can be prepared if required by reaction of polyisocyanates with suitable blocking agents.

The one-component curable composition may be moisture-curing and/or heat-curing.

A "heat-curing composition" in the present document is understood to mean a composition comprising blocked isocyanate groups, in which the blocked isocyanate groups, in the course of heating to a suitable temperature, typically in the range from 120 to 200° C., in special cases even at temperatures from 80° C., are activated to such an extent that crosslinking and hence curing occur with suitable hardeners. This operation is also referred to as baking and is typically effected after the application of the composition.

Typically, the complete curing of the one-component composition described is effected through the action of a combination of moisture and heat.

In a further embodiment, the curable composition has two components.

In the present document, a "two-component" composition is understood to mean a curable composition in which constituents of the composition are present in two separate components which are stored in separate containers and which are each storage-stable. The two components are referred to as component K1 and as component K2. Only just before or during the application of the composition are the two components mixed with one another, and the mixed composition then cures, the curing under some circumstances proceeding or being completed only through the action of moisture and/or heat.

Particular preference is given to two-component curable compositions consisting of a component K1 and a component K2, which compositions comprise at least one polyisocyanate P and at least one aldimine of the formula (I'). In the course of curing thereof, aldehydes ALD1 which have at least two hydroxyl groups and are of the formula (IV') are released, which in turn act as hardeners for the polyisocyanate P and are incorporated covalently into the polymer which forms with chain extension or crosslinking.

Component K1 of the particularly preferred curable two-component composition comprises at least one polyisocyanate P.

In one embodiment, a suitable polyisocyanate P is a polyisocyanate PI in the form of a monomeric di- or triisocyanate or of an oligomer of a monomeric diisocyanate or of a derivative of a monomeric diisocyanate.

Suitable monomeric di- or triisocyanates are, for example, as follows: 1,4-tetramethylene diisocyanate, 2-methylpentamethylene 1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane 1,3- and 1,4-diisocyanate, 1-methyl-2,4- and -2,6-diisocyanatocyclohexane and any mixtures of these isomers (HTDI or $H_6$TDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or $H_{12}$MDI), 1,4-diisocyanato-2,2,6-trimethylcyclohexane (TMCDI), 1,3- and 1,4-bis(isocyanatomethyl)cyclohexane, m- and p-xylylene diisocyanate (m- and p-XDI), m- and p-tetramethyl-1,3- and -1,4-xylylene diisocyanate (m- and p-TMXDI), bis(1-isocyanato-1-methylethyl)naphthalene, dimer and trimer fatty acid isocyanates such as 3,6-bis(9-isocyanatononyl)-4,5-di(1-heptenyl)cyclohexene (dimeryl diisocyanate), α, α, α', α', α", α"-hexamethyl-1,3,5-mesitylene triisocyanate, 2,4- and 2,6-tolylene diisocyanate and any mixtures of these isomers (TDI), 4,4'-, 2,4'- and 2,2'-diphenylmethane diisocyanate and any mixtures of these isomers (MDI), mixtures of MDI and MDI homologues (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), 1,3,5-tris(isocyanatomethyl)benzene, tris(4-isocyanatophenyl)methane and tris(4-isocyanatophenyl)thiophosphate.

Particularly suitable polyisocyanates PI are oligomers or derivatives of monomeric diisocyanates, especially of HDI, IPDI, TDI and MDI. Commercially available types are especially HDI biurets, for example as Desmodur® N 100 and N 3200 (Bayer), Tolonate® HDB and HDB-LV (Rhodia) and Duranate® 24A-100 (Asahi Kasei); HDI isocyanurates, for example as Desmodur® N 3300, N 3600 and N 3790 BA (all from Bayer), Tolonate® HDT, HDT-LV and HDT-LV2 (Rhodia), Duranate® TPA-100 and THA-100 (Asahi Kasei) and Coronate® HX (Nippon Polyurethane); HDI uretdiones, for example as Desmodur® N 3400 (Bayer); HDI iminooxadiazinediones, for example as Desmodur® XP 2410 (Bayer); HDI allophanates, for example as Desmodur® VP LS 2102

(Bayer); IPDI isocyanurates, for example in solution as Desmodur® Z 4470 (Bayer) or in solid form as Vestanat® T1890/100 (Degussa); TDI oligomers, for example as Desmodur® IL (Bayer); and mixed isocyanurates based on TDI/HDI, for example as Desmodur® HL (Bayer). Additionally particularly suitable are room temperature liquid forms of MDI (known as "modified MDI"), which are mixtures of MDI with MDI derivatives, for example MDI carbodiimides or MDI uretonimines or MDI urethanes, known for example under trade names such as Desmodur® CD, Desmodur® PF, Desmodur® PC (all from Bayer), and mixtures of MDI and MDI homologues (polymeric MDI or PMDI), obtainable under trade names such as Desmodur® VL, Desmodur® VL50, Desmodur® VL R10, Desmodur® VL R20 and Desmodur® VKS 20F (all from Bayer), Isonate® M 309, Voranate® M 229 and Voranate® M 580 (all from Dow) or Lupranat® M 10 R (from BASF).

The aforementioned oligomeric polyisocyanates PI are in practice typically mixtures of substances with different degrees of oligomerization and/or chemical structures. They preferably have a mean NCO functionality of 2.1 to 4.0 and contain especially isocyanurate, iminooxadiazinedione, uretdione, urethane, biuret, allophanate, carbodiimide, uretonimine or oxadiazinetrione groups. These oligomers preferably have a low content of monomeric diisocyanates.

Preferred polyisocyanates PI are room temperature liquid forms of MDI, and the oligomers of HDI, IPDI and TDI, especially the isocyanurates.

In a further embodiment, a suitable polyisocyanate P is a polyurethane polymer PUP having isocyanate groups.

In the present document, the term "polymer" firstly embraces a collective of macromolecules which are chemically homogeneous but different in relation to degree of polymerization, molar mass and chain length, which has been prepared by a poly reaction (polymerization, polyaddition, polycondensation). The term secondly also embraces derivatives of such a collective of macromolecules from poly reactions, i.e. compounds which have been obtained by reactions, for example additions or substitutions, of functional groups on given macromolecules, and which may be chemically homogeneous or chemically inhomogeneous. The term further also comprises what are known as prepolymers, i.e. reactive oligomeric preliminary adducts whose functional groups are involved in the formation of macromolecules.

The term "polyurethane polymer" embraces all polymers prepared by what is known as the diisocyanate polyaddition process. This also includes those polymers which are virtually or entirely free of urethane groups. Examples of polyurethane polymers are polyetherpolyurethanes, polyesterpolyurethanes, polyetherpolyureas, polyureas, polyesterpolyureas, polyisocyanurates and polycarbodiimides.

A suitable polyurethane polymer PUP having isocyanate groups is obtainable by the reaction of at least one polyol with at least one polyisocyanate.

The polyols used for the preparation of a polyurethane polymer PUP may, for example, be the following polyols or mixtures thereof:

polyetherpolyols, also known as polyoxyalkylenepolyols or oligoetherols, which are polymerization products of ethylene oxide, 1,2-propylene oxide, 1,2- or 2,3-butylene oxide, tetrahydrofuran or mixtures thereof, possibly polymerized with the aid of a starter molecule, for example water, ammonia, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, and mixtures of the aforementioned compounds. It is possible to use either polyoxyalkylenepolyols which have a low degree of unsaturation (measured to ASTM D-2849-69 and reported in milliequivalents of unsaturation per gram of polyol (meq/g)), prepared, for example, with the aid of double metal cyanide complex catalysts (DMC catalysts), or polyoxyalkylenepolyols with a higher degree of unsaturation, prepared, for example, with the aid of anionic catalysts such as NaOH, KOH, CsOH or alkali metal alkoxides.

Particularly suitable polyetherpolyols are polyoxyalkylenediols and -triols, especially polyoxyalkylenediols. Particularly suitable polyoxyalkylenedi- and -triols are polyoxyethylenedi- and -triols and polyoxypropylenedi- and -triols.

Particularly suitable polyoxypropylenediols and -triols have a degree of unsaturation lower than 0.02 meq/g and a molecular weight in the range from 1000 to 30 000 g/mol, and also polyoxypropylenediols and -triols with a molecular weight of 400 to 8000 g/mol. In the present document, "molecular weight" or "molar mass" is always understood to mean the molecular weight average $M_n$. Especially suitable are polyoxypropylenediols with a degree of unsaturation less than 0.02 meq/g and a molecular weight in the range from 1000 to 12 000, especially between 1000 and 8000 g/mol. Such polyetherpolyols are sold, for example, under the trade name Acclaim® by Bayer.

Likewise particularly suitable are so-called "EO-endcapped" (ethylene oxide-endcapped) polyoxypropylenediols and -triols. The latter are specific polyoxypropylenepolyoxyethylenepolyols which are obtained, for example, by alkoxylating pure polyoxypropylenepolyols with ethylene oxide on completion of the polypropoxylation, and have primary hydroxyl groups as a result.

Styrene-acrylonitrile- or acrylonitrile-methyl methacrylate-grafted polyetherpolyols.

Polyesterpolyols, also known as oligoesterols, prepared by known processes, especially the polycondensation of hydroxycarboxylic acids or the polycondensation of aliphatic and/or aromatic polycarboxylic acids with di- or polyhydric alcohols.

Especially suitable polyesterpolyols are those prepared from di- to trihydric, especially dihydric, alcohols, for example ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimer diol), neopentyl glycol hydroxypivalate, glycerol, 1,1,1-trimethylolpropane or mixtures of the aforementioned alcohols, with organic di- or tricarboxylic acids, especially dicarboxylic acids, or the anhydrides or esters thereof, for example succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic anhydride, isophthalic acid, terephthalic acid, dimethyl terephthalate, hexahydrophthalic acid, trimellitic acid and trimellitic anhydride, or mixtures of the aforementioned acids, and also polyesterpolyols formed from lactones, for example from ε-caprolactone, and starters such as the aforementioned di- or trihydric alcohols.

Particularly suitable polyesterpolyols are polyesterdiols.

Polycarbonatepolyols, as obtainable by reaction, for example, of the abovementioned alcohols—used to form the polyesterpolyols—with dialkyl carbonates such as dimethyl carbonate, diaryl carbonates such as diphenyl carbonate, or phosgene.

Particularly suitable substances are polycarbonatediols.

Likewise suitable as polyols are block copolymers which bear at least two hydroxyl groups and have at least two different blocks with polyether, polyester and/or polycarbonate structure of the type described above.

Polyacrylate- and polymethacrylatepolyols.

Polyhydroxy-functional fats and oils, for example natural fats and oils, especially castor oil; or polyols—known as oleochemical polyols—obtained by chemical modification of natural fats and oils, for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can be derivatized, for example, by hydroformylation and hydrogenation to hydroxy fatty acid esters.

Polyhydrocarbonpolyols, also known as oligohydrocarbonols, for example polyhydroxy-functional polyolefins, polyisobutylenes, polyisoprenes; polyhydroxy-functional ethylene-propylene, ethylene-butylene or ethylene-propylene-diene copolymers, as produced, for example, by Kraton Polymers, polyhydroxy-functional polymers of dienes, especially of 1,3-butadiene, which can especially also be prepared from anionic polymerization; polyhydroxy-functional copolymers of dienes such as 1,3-butadiene or diene mixtures, and vinyl monomers such as styrene, acrylonitrile, vinyl chloride, vinyl acetate, vinyl alcohol, isobutylene and isoprene, for example polyhydroxy-functional acrylonitrile/butadiene copolymers, which can be prepared, for example, from carboxyl-terminated acrylonitrile/butadiene copolymers (commercially available under the Hycar® CTBN name from Noveon) and epoxides or amino alcohols; and hydrogenated polyhydroxy-functional polymers or copolymers of dienes.

These polyols mentioned preferably have a mean molecular weight of 250-30 000 g/mol, especially of 400-20 000 g/mol, and preferably have a mean OH functionality in the range from 1.6 to 3.

In addition to these polyols mentioned, small amounts of low molecular weight di- or polyhydric alcohols, for example 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, for example dimer fatty acid dials, 1,1,1-trimethylolethane, 1,1,1-trimethylolpropane, glycerol, pentaerythritol, low molecular weight alkoxylation products of the aforementioned di- and polyhydric alcohols, and mixtures of the aforementioned alcohols, can be used additionally in the preparation of a polyurethane polymer PUP.

The polyisocyanates used for the preparation of a polyurethane polymer PUP may be aliphatic, cycloaliphatic or aromatic polyisocyanates, especially diisocyanates, for example the monomeric diisocyanates as have already been mentioned as suitable polyisocyanates PI, and also oligomers and polymers of these monomeric diisocyanates, and any desired mixtures of these isocyanates. Preference is given to monomeric diisocyanates, especially MDI, TDI, HDI and IPDI.

A polyurethane polymer PUP is prepared in a known manner directly from the polyisocyanates and the polyols, or by stepwise adduction processes, as also known as chain extension reactions.

In a preferred embodiment, the polyurethane polymer PUP is prepared via a reaction of at least one polyisocyanate and at least one polyol, the isocyanate groups being present in a stoichiometric excess relative to the hydroxyl groups. The ratio between isocyanate and hydroxyl groups is advantageously 1.3 to 10, especially 1.5 to 5.

The reaction is advantageously performed at a temperature at which the polyols and polyisocyanates used and the polyurethane polymer formed are present in liquid form.

The polyurethane polymer PUP has a molecular weight of preferably more than 500 g/mol, especially one between 1000 and 30 000 g/mol.

Moreover, the polyurethane polymer PUP preferably has a mean NCO functionality in the range from 1.8 to 3.

Suitable polyisocyanates P are finally also mixtures comprising a polyurethane polymer PUP and a polyisocyanate PI, especially, on the one hand, mixtures comprising an MDI-based polyurethane polymer PUP and monomeric and/or polymeric MDI, and, on the other hand, mixtures comprising an IPDI-based polyurethane polymer PUP and monomeric and/or oligomeric IPDI.

Component K2 of the particularly preferred curable two-component composition comprises at least one aldimine of the formula (I'). Suitable aldimines for this purpose are the above-described aldimines of the formula (I'), or the preferred embodiments thereof as already described in detail, especially aldimines of the formula (I a) and aldimines of the formula (I b).

Particular preference is given to aldimines of the formula (I') with $R^{4'}$ and $R^{5'}$ radicals which together have two hydroxyl groups.

Component K2 optionally comprises further compounds reactive towards isocyanate groups, such as polyamines, polyols, amino alcohols, polythiols, or further blocked amines.

Suitable polyamines in component K2 are primary aliphatic polyamines as already described as amines B2 of the formula (III b); secondary aliphatic polyamines, for example N,N'-dibutylethylenediamine; N,N'-di-tert-butylethylenediamine, N,N'-diethyl-1,6-hexanediamine, 1-(1-methylethylamino)-3-(1-methylethylaminoethyl)-3,5,5-trimethylcyclohexane (Jefflink® 754 from Huntsman), N4-cyclohexyl-2-methyl-N2-(2-methylpropyl)-2,4-pentanediamine, N,N'-dialkyl-1,3-xylylenediamine, bis(4-(N-alkylamino)cyclohexyl)methane, N-alkylated polyetheramines, for example the Jeffamine® products SD-231, SD-401, SD-404 and SD-2001 (all from Huntsman), products from the Michael-type addition of the primary aliphatic polyamines mentioned by way of example onto Michael acceptors such as maleic diesters, fumaric diesters, citraconic diesters, acrylic esters, methacrylic esters, cinnamic esters, itaconic diesters, vinylphosphonic diesters, aryl vinylsulfonates, vinyl sulphones, vinyl nitriles, 1-nitroethylenes or Knoevenagel condensation products, for example those formed from malonic diesters and aldehydes such as formaldehyde, acetaldehyde or benzaldehyde; aliphatic polyamines with primary and secondary amino groups, for example N-butyl-1,6-hexanediamine; primary and/or secondary aromatic polyamines, for example m- and p-phenylenediamine, 4,4'-diaminodiphenylmethane (MDA), 3,3'-dichloro-4,4'-diaminodiphenylmethane (MOCA), mixtures of 3,5-dimethylthio-2,4- and -2,6-toluylenediamine (obtainable as Ethacure® 300 from Albemarle), mixtures of 3,5-diethyl-2,4- and -2,6-toluylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulphone (DDS), 4-amino-N-(4-aminophenyl)benzenesulfonamide, 5,5'-methylenedianthranilic acid, dimethyl (5,5'-methylenedianthranilate), 1,3-propylenebis(4-aminobenzoate), 1,4-butylenebis(4-aminobenzoate), polytetramethylene oxide bis(4-aminobenzoate) (obtainable as Versalink® from Air Products), 1,2-bis(2-aminophenylthio)ethane, N,N'-dialkyl-p-phenylenediamine, N,N'-dialkyl-4,4'-15 diaminodiphenylmethane, 2-methylpropyl (4-chloro-3,5-diaminobenzoate) and tent-butyl (4-chloro-3,5-diaminobenzoate); and polyamines having more than three amino groups.

Suitable polyols in component K2 are the same polyols as have already been mentioned as suitable for preparing a polyurethane polymer PUP, and those low molecular weight di- or polyhydric alcohols as mentioned above as suitable for additional use in the preparation of a polyurethane polymer PUP.

Suitable amino alcohols in component K2 are compounds which have at least one primary or secondary amino group and at least one hydroxyl group, for example the aliphatic hydroxylamines as already mentioned above as suitable amines B1 for preparing the aldimines of the formula (I), and additionally, for example, diethanolamine, 2-(methylamino)ethanol, 2-(ethylamino)ethanol, 2-(butylamino)ethanol and 2-(cyclohexylamino)ethanol.

Suitable polythiols in component K2 are, for example, liquid mercapto-terminated polymers known under the Thiokol® brand name, for example the products LP-3, LP-33, LP-980, LP-23, LP-55, LP-56, LP-12, LP-31, LP-32 and LP-2 (Morton Thiokol; obtainable, for example, from SPI Supplies, USA, or from Toray Fine Chemicals, Japan), and polyesters of thiocarboxylic acids, for example pentaerythritol tetramercaptoacetate, trimethylolpropane trimercaptoacetate, glycol dimercaptoacetate, pentaerythritol tetra(3-mercaptopropionate), trimethylolpropane tri(3-mercaptopropionate) and glycol di(3-mercaptopropionate).

In addition to the aldimines of the formula (I), it is possible to use further blocked amines as a constituent of component K2, especially ketimines, oxazolidines, enamines and other aldimines. Such other aldimines are obtainable proceeding from aldehydes other than the abovementioned aldehydes ALD1 of the formula (IV'), for example aldehydes ALD of the formula (IV) having only one hydroxyl group, isobutyraldehyde, and the products from the esterification of carboxylic acids as described in WO 2004/013088 A1, especially the products from the esterification of lauric acid with 3-hydroxypivalaldehyde. Ketimines are obtainable, for example, from the reaction of the above-described amines B of the formula (III) with ketones. Suitable oxazolidines are especially polyoxazolidines, for example OZ hardener (Bayer). Suitable enamines are obtainable, for example, from the reaction of amines having a plurality of secondary amino groups with aliphatic or cycloaliphatic aldehydes or ketones which have at least one hydrogen atom on the carbon atom in the α position to the carbonyl group.

In one embodiment, component K2 comprises water. Component K2 comprises especially the amount of water required for hydrolysis of the aldimino groups and other blocked amino groups, or a portion thereof.

The particularly preferred curable two-component composition optionally comprises further constituents, especially assistants and additives used customarily in polyurethane compositions, for example the following:

plasticizers, for example carboxylic esters such as phthalates, for example dioctyl phthalate, diisononyl phthalate or diisodecyl phthalate, adipates, for example dioctyl adipate, azelates and sebacates, organic phosphoric and sulphonic esters or polybutenes;

nonreactive thermoplastic polymers, for example homo- or copolymers of unsaturated monomers, especially from the group comprising ethylene, propylene, butylene, isobutylene, isoprene, vinyl acetate and alkyl (meth)acrylates, especially polyethylenes (PE), polypropylenes (PP), polyisobutylenes, ethylene-vinyl acetate copolymers (EVA) and atactic poly-α-olefins (APAOs);

solvents;

inorganic and organic fillers, for example ground or precipitated calcium carbonates optionally coated with fatty acids, especially stearates, barite (BaSO$_4$, also known as heavy spar), quartz flours, calcined kaolins, aluminium oxides, aluminium hydroxides, silicas, especially finely divided silicas from pyrolysis processes, carbon blacks, especially industrially produced carbon blacks (referred to hereinafter as "carbon black"), PVC powders or hollow spheres;

fibres, for example of polyethylene;

pigments, for example titanium dioxide or iron oxides;

catalysts which accelerate the hydrolysis of aldimines, especially acids, for example organic carboxylic acids such as benzoic acid, salicylic acid or 2-nitrobenzoic acid, organic carboxylic anhydrides such as phthalic anhydride, hexahydrophthalic anhydride and hexahydromethylphthalic anhydride, silyl esters of organic carboxylic acids, organic sulphonic acids such as methanesulphonic acid, p-toluenesulphonic acid or 4-dodecylbenzenesulphonic acid, sulphonic esters, other organic or inorganic acids, or mixtures of the aforementioned acids and acid esters;

catalysts which accelerate the reaction of the isocyanate groups, for example organotin compounds such as dibutyltin diacetate, dibutyltin dilaurate, dibutyltin dichloride, dibutyltin diacetylacetonate and dioctyltin dilaurate, bismuth compounds such as bismuth trioctoate and bismuth tris(neodecanoate), and compounds containing tertiary amino groups, such as 2,2'-dimorpholinodiethyl ether and 1,4-diazabicyclo[2.2.2]octane;

rheology modifiers, for example thickeners or thixotropic agents, for example urea compounds, polyamide waxes, bentonites or fumed silicas;

reactive diluents and crosslinkers, for example monomeric diisocyanates, and also oligomers and derivatives of these polyisocyanates, adducts of monomeric polyisocyanates with short-chain polyols, and also adipic dihydrazide and other dihydrazides, and also polyisocyanates with blocked isocyanate groups, as already mentioned above;

blocked amines, for example in the form of ketimines, oxazolidines, enamines or other aldimines;

desiccants, for example molecular sieves, calcium oxide, high-reactivity isocyanates such as p-tosyl isocyanate, orthoformic esters, alkoxysilanes such as tetraethoxysilane;

organoalkoxysilanes, also referred to hereinafter as "silanes", for example epoxysilanes, (meth)acryloylsilanes, isocyanatosilanes, vinylsilanes, carbamatosilanes, alkylsilanes, S-(alkylcarbonyl)mercaptosilanes and aldiminosilanes, and oligomeric forms of these silanes;

stabilizers against heat, light and UV radiation;

flame-retardant substances;

surface-active substances, for example wetting agents, leveling agents, devolatilizers or defoamers;

biocides, for example algicides, fungicides or substances which inhibit fungal growth.

When such further constituents are used, it is advantageous to ensure that they do not significantly impair the storage stability of the particular component K1 or K2 of the composition. If such additives are present as a constituent of component it should be ensured that they do not trigger the crosslinking of the isocyanate groups to a significant degree during storage. More particularly, this means that additives used in this way should contain at most traces of water, if any. It may be advisable to chemically or physically dry certain additives before they are mixed into component K1.

In the case of component K2, in addition to these, further assistants and additives are additionally possible, which are storable together with free isocyanate groups only briefly, if at all. These are especially catalysts such as:

compounds of zinc, manganese, iron, chromium, cobalt, copper, nickel, molybdenum, lead, cadmium, mercury, antimony, vanadium, titanium, zirconium or potassium, such as zinc(II) acetate, zinc(II) 2-ethylhexanoate, zinc(II) laurate, zinc(II) oleate, zinc(II) naphthenate, zinc(II) acetylacetonate, zinc(II) salicylate, manganese(II) 2-ethylhexanoate, iron(III) 2-ethylhexanoate, iron(III) acetylacetonate, chromium(III) 2-ethylhexanoate, cobalt(II) naphthenate, cobalt(II) 2-ethylhexanoate, copper(II) 2-ethylhexanoate, nickel(II) naphthenate, phenylmercuric neodecanoate, lead(II) acetate, lead(II) 2-ethylhexanoate, lead(II) neodecanoate, lead(II) acetylacetonate, aluminium lactate, aluminium oleate, aluminium (III) acetylacetonate, diisopropoxytitanium bis(ethylacetoacetate), dibutoxytitanium bis(ethylacetoacetate), dibutoxytitanium bis(acetylacetonate), potassium acetate, potassium octoate; tertiary amines, such as triethylamine, tributylamine, N-ethyldiisopropylamine, N,N,N',N'-tetramethylethylenediamine, pentamethyldiethylenetriamine and higher homologues thereof, N,N,N',N'-tetramethylpropylenediamine, pentamethyldipropylenetriamine and higher homologues thereof, N,N,N',N'-tetramethyl-1,3-butanediamine, N,N,N',N'-tetramethyl-1,6-hexanediamine, bis(dimethylamino)methane, N,N-dimethylbenzylamine, N,N-dimethylcyclohexylamine, N-methyldicyclohexylamine, N,N-dimethylhexadecylamine, bis(N,N-diethylaminoethyl) adipate, N,N-dimethyl-2-phenylethylamine, tris(3-dimethylaminopropyl)amine, 1,4-diazabicyclo[2.2.2]octane (DABCO), 1,8-diazabicyclo[5.4.0]undec-7-ene (DBU), 1,5-diazabicyclo[4.3.0]non-5-ene (DBN), N-methylmorpholine, N-ethylmorpholine, N-cocomorpholine, N,N'-dimethylpiperazine, N-methyl-N'-dimethylaminoethylpiperazine, bis (dimethylaminoethyl)piperazine, 1,3,5-tris(dimethylaminopropyl)-hexahydrotriazine or bis(2-dimethylaminoethyl) ether; aromatic nitrogen compounds, such as 4-dimethylaminopyridine, N-methylimidazole, N-vinylimidazole or 1,2-dimethylimidazole; amidines and guanidines, such as 1,1,3,3-tetramethylguanidine; tertiary amines containing active hydrogen atoms, such as triethanolamine, triisopropanolamine, N-methyldiethanolamine, N,N-dimethylethanolamine, 3-(dimethylamino)propyldiisopropanolamine, bis(3-(dimethylamino)propyl) isopropanolamine, bis(3-dimethylaminopropyl)amine, 3-(dimethylamino)propylurea, Mannich bases of phenols such as 2,4,6-tris(dimethylaminomethyl)phenol or 2,4,6-tris (3-(dimethylamino)propylaminomethyl)phenol, imidazoles, for example N-hydroxypropylimidazole, N-(3-aminopropyl) imidazole, and alkoxylation and polyalkoxylation products of these compounds, for example dimethylaminoethoxyethanol; organic ammonium compounds, such as benzyltrimethylammonium hydroxide, or alkoxylated tertiary amines; "delayed action" catalysts, which are modifications of known metal or amine catalysts, such as reaction products of tertiary amines and carboxylic acids or phenols, for example of 1,4-diazabicyclo[2.2.2]octane or DBU and formic acid or acetic acid; and combinations of the compounds mentioned, especially of metal compounds and tertiary amines.

The composition preferably comprises at least one catalyst in the form of an organometallic compound and/or of a tertiary amine and/or of an acid, especially of an organic carboxylic acid or sulphonic acid.

The two components K1 and K2 are prepared separately from one another, for component K1 with the exclusion of moisture. The two components K1 and K2 are storage-stable separately from one another, i.e. they can each be stored in a suitable package or arrangement, for example a drum, a pouch, a bucket, a cartridge or a bottle, over several months up to one year and longer before use, without their particular properties changing to a degree relevant for the use thereof.

For use of the two-component composition, the two components K1 and K2 are mixed with one another. It should be ensured that the mixing ratio is selected such that the constituents reactive towards isocyanate groups are in a suitable ratio to the isocyanate groups of component K1. More particularly, the ratio is 0.1 to 1.1, preferably 0.5 to 0.95, more preferably 0.6 to 0.9, equivalents of the sum of the hydroxyl groups, amino groups, mercapto groups and protected amino groups present per equivalent of isocyanate groups, protected amino groups in the form of oxazolidino groups being counted double. In the course of curing, excess isocyanate groups react with moisture, especially with air humidity.

The two components K1 and K2 are mixed by a suitable process, for example by means of a static mixer. The mixing can be effected continuously or batchwise. The mixed composition is then applied to a substrate, optionally by means of a suitable application aid. In doing so, it has to be ensured that not too much time passes between the mixing of the components and the application, since excessive preliminary reaction of the constituents of the mixed composition before application can disrupt the function of the cured composition, for example by virtue of the adhesion to the substrate being built up only in an inadequate or retarded manner. The maximum period of time within which the mixed composition should be applied is referred to as "pot life".

After the mixing of components K1 and K2, the curing commences. The aldimino groups begin to react with the isocyanate groups in the manner already described as soon as they come into contact with water. Either the water is already present in the mixed composition—by virtue of it having been a constituent of component K2, or by virtue of it having been added to the composition before or during the mixing of the two components K1 and K2—or the water diffuses into the mixed composition in the form of air humidity. In the latter case, the aldimino groups react with the isocyanate groups from the outside inwards, parallel to the penetration of the moisture from the air into the composition. As already described, the reaction of the isocyanate groups with the aldimino groups being hydrolyzed need not necessarily proceed via free amino groups, but can also proceed via intermediates of the hydrolysis reaction. In the same way, the reactive groups of further blocked amines which may be present in the composition are released. In addition, after the mixing of components K1 and K2, the hydroxyl, mercapto and amino groups present in the composition react with the isocyanate groups. The hydroxyl groups present on the $R^{4'}$ and $R^{5'}$ radicals can react with the isocyanate groups before, during or after the formal release of the aldehyde ALD1. As a result of these reactions, the mixed composition crosslinks and ultimately cures to give a solid material.

The curing of the curable compositions described generally proceeds without the formation of bubbles, even at high curing rate. The curing rate can be influenced via the type and amount of one or more catalysts which may be present, via the temperature which exists in the course of curing and via the air humidity or the amount of water added.

The curable compositions described have a series of advantages.

The aldimines of the formula (I') contain sterically hindered aldimino groups which are not tautomerizable to enamino groups. These react in the presence of water with isocyanate groups, in a formal sense, as primary amino groups, their reactivity being greatly reduced compared to the corresponding free primary amino groups, such that such systems have an efficiently manageable curing rate.

The presence of the aldimines prevents the direct, carbon dioxide ($CO_2$)-producing reaction of the isocyanate groups with moisture which is already present in the composition or gets into the composition after application, and hence substantially suppresses the formation of undesired gas bubbles in the course of curing of the composition.

Moreover, the aldehydes ALD1 of the formula (IV') released from the aldimines of the formula (I') in the course of curing themselves act as hardeners, since they bear, on the $R^{4'}$ and $R^{5'}$ radicals together, at least two hydroxyl groups and therefore react with the isocyanate groups with chain extension or crosslinking of the polyurethane polymer which forms and do not lead to chain terminations. The covalent incorporation of the aldehydes ALD1 into the polymer in this manner is particularly valuable, since it avoids the problems that unincorporable aldehydes can cause in the cured composition, such as especially shrinkage, unpleasant odours, sweating or reduced mechanical strength and durability.

In addition, the aldimines of the formula (I'), owing to their content of tertiary amino groups, can exert a catalytic effect on the reaction of the isocyanate groups and thus accelerate the curing. This accelerating effect is additionally promoted by the fact that the tertiary amino groups in the aldehyde moiety of the aldimines, i.e. after the hydrolysis thereof, are localized in the aldehydes ALD1 released. However, it is advantageous that the basicity of these tertiary amino groups is comparatively low, since strongly basic tertiary amines can disrupt the acid-catalyzed hydrolysis of the aldimino groups and/or excessively accelerate the direct reaction of the isocyanate groups, especially with water, which can result in incomplete curing. The tertiary amino groups are localized in the aldehyde moiety of the aldimines of the formula (I') and are incorporated covalently into the polymer which forms in the course of curing through the reaction of the hydroxyl groups with isocyanate groups. After the incorporation into the polymer, the catalytic activity of the tertiary amino group is significantly reduced owing to the restricted mobility thereof, which may be advantageous for the durability of the material.

The aldehyde groups which form in the course of hydrolysis of the aldimino groups are preserved in the course of curing and are covalently incorporated into the polymer which forms via the reactions described. They can, if desired, be used for further reactions.

A further advantage of the compositions described lies in the comparatively low odour of the aldimines of the formula (I) described, and of the aldehydes ALD1. As a result, the compositions have only a low odour, if any, before, during and after the curing.

Preferred applications of the curable compositions described are adhesives, sealants, potting compositions, coatings, floor coverings, paints, coating materials, primers or foams. Some applications will be described briefly hereinafter, which, however, is in no way intended to restrict another use of these compositions.

In a preferred embodiment, one of the curable compositions described is used as an adhesive or sealant. In this application, the curable composition advantageously comprises at least one filler, which influences both the rheological properties of the uncured composition and the mechanical properties and the surface characteristics of the cured composition. Suitable fillers are the inorganic and organic fillers already mentioned. Preference is given to carbon black, calcium carbonates, calcined kaolins, finely divided silicas, PVC powder and flame-retardant fillers such as hydrates or hydroxides, especially aluminium hydroxide. The filler content is especially in the range from 10 to 70% by weight, preferably from 20 to 60% by weight, based on the overall composition. It may be advantageous to use a mixture of different fillers.

In addition, the curable composition in the application as an adhesive or sealant advantageously comprises at least one of the catalysts already mentioned, which accelerate the hydrolysis of the aldimino groups or the reaction of the isocyanate groups. Especially suitable are mixtures of organic acids and an organometallic compound or a metal complex, of an organic acid and a compound containing tertiary amino groups, or mixtures of organic acids, an organometallic compound or a metal complex, and a compound containing tertiary amino groups. A typical content of catalysts is 0.005 to 2% by weight based on the overall composition, it being clear to the person skilled in the art what amounts used are advisable for which catalysts.

An adhesive or sealant is produced and applied in the manner already described.

Suitable applications of an adhesive are, for example, the bonding of components in construction or civil engineering and in the manufacture or repair of industrial goods or consumer goods, especially of windows, domestic appliances or modes of transport such as water or land vehicles, preferably automobiles, buses, trucks, trains or ships, and the bonding of articles in the furniture, textile or packaging industry; or the sealing of joints, seams or cavities in industrial manufacture or repair, or in construction or civil engineering.

Suitable applications of a sealant are, for example, the sealing of a built structure, especially joints in construction or civil engineering, or the sealing of part of a built structure, for example of a window or of a floor, or the sealing of an industrial good, for example of a domestic appliance or of a mode of transport, especially a water or land vehicle, or of a part thereof.

In the cured state, the adhesive or sealant typically has elastic properties.

In a further preferred embodiment, one of the curable compositions described is used as a coating. In this application, the curable composition advantageously comprises at least one filler, which influences both the rheological properties of the uncured composition, and the mechanical properties and the surface characteristics of the cured composition. Suitable fillers are the inorganic and organic fillers already mentioned. Preference is given to calcium carbonates, barite and quartz flours, and flame-retardant fillers such as hydrates or hydroxides, especially aluminium hydroxide. The filler content is especially in the range from 10 to 70% by weight, preferably from 20 to 60% by weight, based on the overall composition. It may be advantageous to use a mixture of different fillers.

In addition, the curable composition in the application as a coating advantageously comprises at least one catalyst. Suitable catalysts are the same catalysts in the same amounts as already mentioned as suitable constituents of adhesives and sealants.

In addition, the curable composition in the application as a coating advantageously comprises at least another of the assistants and additives already mentioned, especially selected from the group comprising pigments, solvents, leveling agents, defoamers and stabilizers.

Suitable solvents are, for example, ketones such as acetone, methyl ethyl ketone, methyl isobutyl ketone, diisobutyl ketone and mesityl oxide, and cyclic ketones such as cyclohexanone and methylcyclohexanone; esters such as methyl acetate, ethyl acetate, propyl acetate, butyl acetate, tert-butyl acetate, formates, propionates or malonates; ethers such as ketone ethers, ester ethers and dialkyl ethers such as diisopropyl ether, diethyl ether, dibutyl ether, methyl tert-butyl ether, diethylene glycol diethyl ether and ethylene glycol diethyl ether; aliphatic and aromatic hydrocarbons such as toluene, xylene, heptane, octane, and mineral oil fractions such as naphtha, white spirit, petroleum ether or benzine; halogenated hydrocarbons such as methylene chloride; and N-alkylated lactams, for example N-methylpyrrolidone, N-cyclohexylpyrrolidone or N-dodecylpyrrolidone. The solvents content is especially in the range from 0 to 30% by weight, preferably 0 to 20% by weight, based on the overall composition.

A coating is produced and applied in the manner already described. It advantageously has a fluid consistency with good leveling properties. As a result, it can be applied in a simple manner as a self-leveling coating to predominantly flat surfaces, for example as a floor covering. The two components K1 and K2 are mixed with one another in a suitable manner before application, and the mixed composition is applied within the pot life.

The curable composition is applied in the form of a coating typically by pouring it onto the substrate to be coated and is distributed homogeneously in the liquid state with the aid, for example, of a coating knife or of a notched trowel. In addition, the material can be leveled and deaerated with a spiked roller. However, machine application is also possible, for example in the form of a spray application.

A suitable substrate to which the composition is typically applied is, for example, concrete, cement, asphalt, steel, wood, ceramic or a plastic, which substrate can be pretreated by cleaning, brushing or sandblasting, and/or may have a primer. Examples of useful primers include adhesion promoter solutions.

A "primer" is understood in the present document to mean a composition which is suitable as an undercoat and comprises, as well as nonreactive volatile substances and optionally solid additives, at least one polymer and/or at least one substance with reactive groups, and which is capable of curing, when applied to a substrate, to give a solid film with good adhesion in a layer thickness of typically at least 5 µm, the curing resulting either solely through the evaporation of the nonreactive volatile substances, for example solvents or water, or through a chemical reaction, or through a combination of these factors, and which builds up good adhesion to a layer applied subsequently, for example an adhesive or sealant.

A finished floor covering is frequently a construction composed of several different layers. A typical construction may begin, for example, with a primer which has the task of preparing the substrate for the polyurethane coating. Subsequently, for example, the composition described, which typically has elastic properties in the cured state, is applied, which application can be effected in one or more steps according to the nature of the substrate and desired layer thickness. Typically, a layer thickness of 0.5 to 3 mm, especially 0.5 to 2 mm, is applied per layer. Finally, a seal can subsequently be applied, which also influences the surface characteristics of the floor covering in a thin layer, for example in a thickness of a few micrometers to a few tenths of a millimeter. This may be a transparent or pigmented seal.

The coating described can advantageously be used in the interior or exterior of a building or of a built structure, for example as a floor covering for interiors such as offices, industrial halls, gymnasiums or chill rooms, or outdoors for balconies, terraces, bridges, parking decks, or sports grounds and playgrounds.

A further aspect of the present invention relates to a process for bonding a substrate S1 to a substrate S2, which comprises the steps of
  i) applying an above-described curable composition to a substrate S1;
  ii) contacting the applied composition with a substrate S2 within the open time of the composition;
  or
  i') applying an above-described composition to a substrate S1 and to a substrate S2;
  ii') contacting the applied compositions with one another within the open time of the composition;
  the substrate S2 consisting of the same material as, or a different material than, the substrate S1.

A further aspect of the present invention relates to a process for sealing. This comprises the step of
  i") applying an above-described curable composition between a substrate S1 and a substrate S2, such that the composition is in contact with the substrate S1 and the substrate S2;
  the substrate S2 consisting of the same material as, or a different material than, the substrate S1.

Typically, the sealant is injected into a joint.

A further aspect of the present invention relates to a process for coating a substrate S1. This comprises the step of
  i''') applying an above-described curable composition to a substrate S1 within the open time of the composition In these three processes, suitable substrates S1 and/or S2 are, for example, inorganic substrates such as glass, glass ceramic, concrete, mortar, brick, tile, gypsum and natural stones such as granite or marble; metals or alloys such as aluminium, steel, nonferrous metals, galvanized metals; organic substrates such as leather, fabrics, paper, wood, resin-bound woodbase materials, resin-textile composite materials, plastics such as polyvinyl chloride (rigid and flexible PVC), acrylonitrile-butadiene-styrene copolymers (ABS), SMC (sheet moulding composites), polycarbonate (PC), polyamide (PA), polyesters, PMMA, polyesters, epoxy resins, polyurethanes (PU), polyoxymethylene (POM), polyolefins (PO), especially surface-plasma-, -corona- or -flame-treated polyethylene (PE) or polypropylene (PP), ethylene/propylene copolymers (EPM) and ethylene/propylene-diene terpolymers (EPDM); coated substrates such as powder-coated metals or alloys; and paints and coating materials, especially automotive coating materials.

The substrates can be pretreated if required before the application of the composition. Such pretreatments include especially physical and/or chemical cleaning processes, for example grinding, sandblasting, brushing or the like, or treatment with detergents or solvents, or the application of an adhesion promoter, of an adhesion promoter solution or of a primer.

In the case of a two-component composition, the two components K1 and K2 are mixed with one another just before the application.

In the case of a heat-curing composition, the composition applied is then baked onto the adhesive bond, the seal or the coating, by heating it to a suitable temperature.

The curable composition can be applied within a broad temperature spectrum. For example, the composition can be applied at room temperature, as is typical of an adhesive or a sealant. The composition can, however, also be applied at lower or else higher temperatures. The latter is advantageous especially when the composition comprises high-viscosity or meltable components as are typically present in meltable adhesives, for example warm-melt adhesives or hot-melt adhesive. The application temperatures for warm-melts are, for example, in the range from 40 to 80° C., in the case of hot-melts in the range from 85 to 200° C.

These described processes for adhesive bonding, sealing or coating—or the use of one of the compositions described as an adhesive, sealant, potting composition, coating, floor covering, paint, coating material, primer or foam—give rise to an article.

This article is especially a built structure, especially a built structure in construction or civil engineering, or an industrial good or a consumer good, especially a window, a domestic appliance, or a mode of transport, especially a water or land vehicle, preferably an automobile, a bus, a truck, a train or a ship, or an installable component of a mode of transport, or an article in the furniture, textile or packaging industry.

EXAMPLES

1. Description of the Measurement Methods

The viscosity was measured on a Physica UM thermostated cone-plate viscometer (cone diameter 20 mm, cone angle 1°, cone tip-plate distance 0.05 mm, shear rate 10 to 1000 s$^{-1}$).

The amine content, i.e. the total content of free amino groups and blocked amino groups (aldimino groups) in the compounds prepared, was determined by titrimetric means (with 0.1N HClO$_4$ in glacial acetic acid, against crystal violet) and is always reported in mmol N/g.

The pK$_a$ for the conjugated acid of a Mannich base was determined approximately using the half-neutralization potential in the potentiometric titration of approx. 1 mmol of Mannich base in 50 ml of water with 0.1N HCl.

Infrared spectra were measured on a Perkin-Elmer 1600 FT-IR instrument as undiluted films on a horizontal ATR measurement unit with a ZnSe crystal; the absorption bands are reported in wavenumbers (cm$^{-1}$) (measurement window: 4000-650 cm$^{-1}$); the addition sh indicates a band which appears as a shoulder, the addition br a broad band.

GC-MS was carried out under the following conditions: Optima-5-MS column, 30 m×0.25 mm, film thickness 0.5 µm; heating rate 15° C./min from 60° C. to 320° C., then held at 320° C. for 15 min; He carrier gas, 14 psi; split 15 ml/min; EI$^+$ ionization method. For the gas chromatogram, the retention time of the product signal (t$_R$) is reported. In the mass spectrum, only the largest peaks are reported (as m/z); the relative intensity (in %) and, if possible, tentative assignment of the molecular fragment are in brackets.

2. Preparation of Aldehydes

3-(N-Bis(2-hydroxyethyl)amino)-2,2-dimethylpropanal

A round-bottom flask under a nitrogen atmosphere was initially charged with 83.4 g (1.00 mol) of 36% aqueous formaldehyde and 75.7 g (1.05 mol) of isobutyraldehyde. With good stirring and ice cooling, 105.1 g (1.00 mol) of diethanolamine were slowly added dropwise from a dropping funnel, while ensuring that the temperature of the reaction mixture did not rise above 20° C. On completion of addition, the mixture was left to stir for one hour at room temperature. The resulting clear, colourless reaction mixture was stirred under reflux in an oil bath at 80° C. over 2 hours and cooled to room temperature, and the volatile constituents were distilled off in a water jet vacuum at 80° C. This gave 181.2 g (96% of theory) of crude product as a clear, yellowish oil, which had an amine content of 5.40 mmol N/g and a viscosity of 23.7 Pa·s at 20° C. The crude product contained, as well as 3-(N-bis(2-hydroxyethyl)amino)-2,2-dimethyl-propanal, smaller proportions of 3-hydroxy-2,2-dimethylpropanal, N-(2-hydroxyethyl)oxazolidine and N-(2-hydroxyethyl)-2-isopropyloxazolidine (according to GC-MS analysis).

pK$_a$≈7.1.

IR: 3358br(OH), 2950, 2929sh, 2913, 2870, 2830, 2719sh br (CHO), 1721 (C═O), 1464, 1391, 1359, 1302br, 1206, 1147, 1078sh, 1037, 966, 940, 920, 883, 786.

GC-MS: t$_R$=10.3 min; mass spectrum: 189 (2, [M]$^+$), 172 (3, [M—OH]$^+$), 158 (11, [M—CH$_2$OH]$^+$), 128 (4), 118 (100, [M—C(CH$_3$)$_2$CHO]$^+$), 116 (15), 102 (6), 98 (5), 88 (2, [118—CHOH]$^+$), 88 (72), 86 (21), 74 (50), 56 (51).

3-(N-Bis(2-hydroxy-2-methylethyl)amino)-2,2-dimethylpropanal

Under the same conditions as described above for the preparation of 3-(N-bis(2-hydroxyethyl)amino)-2,2-dimethylpropanal, 83.4 g (1.00 mol) of 36% aqueous formaldehyde were reacted with 75.7 g (1.05 mol) of isobutyraldehyde and 133.2 g (1.00 mol) of diisopropanolamine, and worked up. This gave 199.4 g (92% of theory) of crude product as a clear, yellowish oil, which had an amine content of 4.87 mmol N/g and a viscosity of 8.2 Pa·s at 20° C. The crude product contained, as well as 3-(N-bis(2-hydroxy-2-methylethyl)amino)-2,2-dimethylpropanal, smaller proportions of 3-hydroxy-2,2-dimethylpropanal, N-(2-hydroxy-2-methylethyl)oxazolidine and N-(2-hydroxy-2-methylethyl)-2-isopropyloxazolidine (according to GC-MS analysis).

pK$_a$≈7.1.

IR: 3392br (OH), 2966, 2933, 2872, 2818, 2719sh br (CHO), 1722 (C═O), 1461, 1409, 1375, 1328, 1274, 1209, 1158, 1130, 1090sh, 1055, 1028sh, 978, 945, 914, 891, 864, 839, 818, 786.

GC-MS: t$_R$=10.3 min; mass spectrum: 217 (3, [M]$^+$), 172 (30, [M—CH(CH$_3$)OH]$^+$), 146 (44, [M-C(CH$_3$)$_2$CHO]$^+$), 144 (21), 130 (6), 126 (6), 116 (7), 114 (10), 102 (100, [146—C(CH$_3$)OH]$^+$), 100 (18), 88 (16), 70 (38).

3. Preparation of Aldimines

Example 1

Aldimine A-1

In a round-bottom flask under a nitrogen atmosphere, 68.2 g of polyetherdiamine (polyoxypropylenediamine with a mean molecular weight of approx. 240 g/mol; Jeffamine® D-230, Huntsman; amine content 8.29 mmol N/g) and 117.6 g of 3-(N-bis(2-hydroxyethyl)amino)-2,2-dimethylpropanal were weighed, and the mixture was stirred at room temperature for one hour. Thereafter, the volatile constituents were removed under reduced pressure (10 mbar, 80° C.). Yield: 177.1 g of a clear, yellow oil with an amine content of 6.78 mmol N/g and a viscosity of 9.8 Pa·s at 20° C.

IR: 3391br (OH), 2964, 2926, 2868, 1662 (C=N), 1469, 1456sh, 1392sh, 1373, 1294, 1106sh, 1049, 1004sh, 926, 903, 877.

Example 2

Aldimine A-2

Under the same conditions as described in example 1, 27.2 g of isophoronediamine (Vestamin® IPD, Degussa; amine content 11.67 mmol N/g) and 71.8 g of 3-(N-bis(2-hydroxy-2-methylethyl)amino)-2,2-dimethylpropanal were reacted. Yield: 93.2 g of a clear, yellow honey with an amine content of 7.66 mmol N/g and a viscosity of 150 Pa·s at 20° C.

IR: 3393br (OH), 2962, 2926, 2898, 2868, 2837, 2818, 1662 (C=N), 1459, 1408, 1373, 1364, 1333, 1273, 1159, 1133, 1116sh, 1058, 1003, 976sh, 945, 909, 891sh, 864, 838.

Example 3

Aldimine A-3

Under the same conditions as described in example 1, 37.7 g of polyetherdiamine (polyoxypropylenediamine with a mean molecular weight of approx. 240 g/mol; Jeffamine® D-230, Huntsman; amine content 8.29 mmol N/g) and 70.6 g of 3-(N-bis(2-hydroxy-2-methylethyl)amino)-2,2-dimethyl-propanal were reacted. Yield: 103.4 g of a clear, yellow-brownish oil with an amine content of 6.26 mmol N/g and a viscosity of 4.0 Pa·s at 20° C.

IR: 3419br (OH), 2965, 2925, 2918, 2868, 2822sh, 1662 (C=N), 1457, 1408sh, 1373, 1331, 1274, 1196sh, 1106, 1089, 1059, 1019, 1002, 977, 944, 910, 865, 838.

Example 4

Aldimine A-4

Under the same conditions as described in example 1, 6.55 g of 2-(2-aminoethoxy)ethanol (DGA; Diglycolamine® Agent, Huntsman; amine content 9.39 mmol N/g) and 13.36 g of 3-(N-bis(2-hydroxyethyl)amino)-2,2-dimethyl-propanal were reacted. Yield: 16.25 g of a clear, yellow oil with an amine content of 7.18 mmol N/g and a viscosity of 3.4 Pa·s at 20° C.

IR: 3358br (OH), 2928, 2865, 2716sh, 1943br, 1663 (C=N), 1467, 1459, 1391, 1358, 1285, 1238, 1123, 1044, 1003sh, 940sh, 924sh, 890, 815, 785, 770.

Comparative Example 5

Aldimine A-5

A round-bottom flask under a nitrogen atmosphere was initially charged with 74.3 g (0.26 mol) of distilled 2,2-dimethyl-3-lauroyloxypropanal. With vigorous stirring, 30.0 g (0.25 mol N) of polyetherdiamine (polyoxypropylenediamine with a mean molecular weight of approx. 240 g/mol; Jeffamine® D-230, Huntsman; amine content 8.29 mmol N/g) were slowly added dropwise from a heated dropping funnel, in the course of which the mixture heated up and became increasingly cloudy. Thereafter, the volatile constituents were removed under reduced pressure (10 mbar, 80° C.). Yield: 99.5 g of a clear, pale yellow oil with an amine content of 2.50 mmol N/g.

4. Preparation of Curable Compositions

Examples 6 to 9 and Comparative Examples 10 and 11

2K Potting Compositions

For each example, the particular constituents of component K2 according to table 1 were weighed in the parts by weight specified, without preceding drying, into a screwtop polypropylene beaker, and mixed by means of a centrifugal mixer (SpeedMixer™ DAC 150, FlackTek Inc.; 2 min at 3000 rpm) to give a homogeneous cream. To this were added the parts by weight of PMDI specified in table 1 as component K1, and mixed in (30 sec at 3000 rpm). The ratio between the isocyanate groups of component K1 and the sum of the reactive groups (hydroxyl and aldimino groups) of component K2 is always 1.1.

TABLE 1

Composition of the two-component potting compositions.

| | Example | | | | | |
|---|---|---|---|---|---|---|
| | 6 | 7 | 8 | 9 | 10 (comp.) | 11 (comp.) |
| Component K1: | | | | | | |
| PMDI[a] | 35.0 | 35.4 | 34.4 | 38.0 | 28.9 | 29.7 |
| Component K2: | | | | | | |
| castor oil[b] | 22.5 | 22.5 | 22.5 | 22.5 | 22.5 | 22.5 |
| dimer fatty acid diol[c] | 17.5 | 17.5 | 17.5 | 17.5 | 17.5 | 22.5 |
| triol[d] | 4.75 | 4.75 | 4.75 | 4.75 | 4.75 | 4.75 |
| aldimine | A-1, 5.0 | A-2, 5.0 | A-3, 5.0 | A-4, 5.0 | A-5, 5.0 | — |
| acid catalyst[e] | 0.25 | 0.25 | 0.25 | 0.25 | 0.25 | 0.25 |
| chalk[f] | 50.0 | 50.0 | 50.0 | 50.0 | 50.0 | 50.0 |

[a]Desmodur® VKS 20 F, Bayer; NCO content = 30.0% by wt.
[b]OH number = 165 mg KOH/g.
[c]Sovermol® 908, Cognis; OH number = 200 mg KOH/g.
[d]Desmophen® 4011 T, Bayer; OH number = 550 mg KOH/g.
[e]salicylic acid (5% by wt. in dioctyl adipate).
[f]Omyacarb® 5-GU, Omya.

The potting compositions thus obtained were tested for curing rate, mechanical properties and bubble formation.

Indications of the curing rate were obtained firstly by measuring the tack-free time. To this end, a small portion of the composition, immediately after mixing, was applied to paperboard in a layer thickness of approx. 2 mm and the time taken, under standard climatic conditions (23±1° C., 50±5% relative air humidity), when the surface of the composition was tapped lightly using an LDPE pipette, for no residues to remain any longer on the pipette for the first time was determined. Secondly, the later curing was monitored by periodically measuring the Shore D hardness to DIN 53505.

To test the mechanical properties, the potting composition was cast as a film with a layer thickness of approx. 2 mm into a planar PTFE mould, and the film was cured under standard climatic conditions for 7 days and tested to DIN EN 53504 for tensile strength, elongation at break and modulus of elasticity (at 0.5-3.0% extension, pulling speed: 10 mm/min).

Bubble formation was assessed qualitatively with reference to the amount of bubbles which occurred in the course of curing of a film with a layer thickness of 2 mm under standard climatic conditions.

The results of these tests are listed in table 2.

TABLE 2

Properties of the two-component potting compositions.

| | Example | | | | | |
|---|---|---|---|---|---|---|
| | 6 | 7 | 8 | 9 | 10 (comp.) | 11 (comp.) |
| Tack-free time (min)[a] | 21 | 19 | 18 | 42 | 58 | 48 |
| Shore D after 1 day | 81 | 78 | 83 | 78 | 60 | 60 |
| Shore D after 3 days | 93 | 93 | 89 | 87 | 73 | 75 |
| Shore D after 7 days | 93 | 94 | 93 | 93 | 84 | 82 |
| Shore D after heat treatment[b] | 93 | 96 | 93 | 94 | 86 | 85 |
| Tensile strength (MPa) | 23.4 | 26.7 | 25.5 | 13.7 | 11.0 | 8.1 |
| Elongation at break (%) | 6 | 3 | 5 | 23 | 75 | 60 |
| Modulus of elasticity (MPa) | 580 | 780 | 615 | 290 | 85 | 100 |
| Bubble formation | none | none | none | none | none | many |

[a]tack-free time.
[b]4 h at 105° C., specimen cured for 7 days under standard climatic conditions.

Examples 12 to 14

Semistructural 2K Adhesives

For each example, the particular constituents of component K2 according to table 3 were weighed in the parts by weight specified, without preceding drying, into a screwtop polypropylene beaker, and mixed by means of a centrifugal mixer (SpeedMixer™ DAC 150, FlackTek Inc.; 2 min at 3000 rpm) to give a homogeneous cream. To this were added the parts by weight of PMDI specified in table 3 as component K1, and mixed in (30 sec at 3000 rpm). The ratio between the isocyanate groups of component K1 and the sum of the reactive groups (hydroxyl and aldimino groups) of component K2 is always 1.1.

TABLE 3

Composition of the semistructural two-component adhesives.

| Example | 12 | 13 | 14 |
|---|---|---|---|
| Component K1: | | | |
| PMDI[a] | 24.5 | 28.0 | 19.0 |
| Component K2: | | | |
| castor oil[b] | 22.4 | 22.4 | 22.4 |
| PPG 1000[c] | 22.4 | 22.4 | 22.4 |
| triol[d] | 2.25 | 2.25 | 2.25 |
| aldimine | A-1, 5.0 | A-2, 5.0 | A-3, 5.0 |
| acid catalyst[e] | 0.25 | 0.25 | 0.25 |
| chalk[f] | 50 | 50 | 50 |

[a]Desmodur ® VKS 20 F, Bayer; NCO content = 30.0% by wt.
[b]OH number = 165 mg KOH/g.
[c]Desmophen ® 1112 BD, Bayer; OH number = 112 mg KOH/g.
[d]Desmophen ® 4011 T, Bayer; OH number = 550 mg KOH/g.
[e]salicylic acid (5% by wt. in dioctyl adipate).
[f]Omyacarb ® 5-GU, Omya.

The adhesives thus obtained were tested for curing rate, mechanical properties and bubble formation as described in example 6. The results of the tests are listed in table 4.

TABLE 4

Properties of the semistructural two-component adhesives.

| Example | 12 | 13 | 14 |
|---|---|---|---|
| Tack-free time (min)[a] | 28 | 38 | 42 |
| Shore D after 1 day | 65 | 73 | 62 |
| Shore D after 3 days | 77 | 81 | 74 |
| Shore D after 7 days | 82 | 86 | 82 |
| Shore D after heat treatment[b] | 84 | 87 | 86 |
| Tensile strength (MPa) | 10.9 | 13.1 | 10.2 |
| Elongation at break (%) | 42 | 25 | 43 |
| Modulus of elasticity (MPa) | 109 | 186 | 100 |
| Bubble formation | none | none | none |

[a]tack-free time in minutes.
[b]4 h at 105° C., specimen cured for 7 days under standard climatic conditions.

Examples 15 and 16

Elastic Two-Component Coatings

For Example for Floor Covering

For each example, the particular constituents of component K1 according to table 5 were weighed in the parts by weight specified, without preceding drying, into a polypropylene cartridge, and mixed by means of a centrifugal mixer (SpeedMixer™ DAC 150, FlackTek Inc.; 30 sec at 2500 rpm). To this were added the parts by weight of the aldimine specified in table 4 as component K2, and mixed in (30 sec at 2500 rpm). The ratio between the isocyanate groups of component K1 and the sum of the reactive groups (hydroxyl and aldimino groups) of component K2 is always 1.1.

The polyurethane polymer was prepared as follows:

1060 g of polyoxypropylenediol (Desmophen® 1111 BD, Bayer; OH number 111.4 mg KOH/g), 650 g of polyoxypropylenediol (Desmophen® 2061 BD, Bayer; OH number 56.1 mg KOH/g), 770 g of isophorone diisocyanate (Vestanat® IPDI, Degussa) and 0.25 g of dibutyltin dilaurate were reacted at 80° C. to give an NCO-terminated polyurethane polymer with a content of free isocyanate groups of 6.8% by weight.

TABLE 5

Composition of the two-component coatings.

| Example | 15 | 16 |
|---|---|---|
| Component K1: | | |
| polyurethane polymer 1 | 64.0 | 64.0 |
| IPDI trimer[a] | 32.0 | 32.0 |
| acid catalyst[b] | 1.0 | 1.5 |
| amine catalyst[c] | 0.5 | 0.5 |
| tin catalyst[d] | 1.0 | 1.0 |
| defoamer[e] | 1.5 | 1.5 |
| Component K2: | | |
| aldimine | A-2, 13.6 | A-3, 15.3 |

[a]45% by wt. of IPDI trimer (Vestanat ® T 1890/100, Degussa; NCO content = 17.3% by wt.) in xylene.
[b]5% by wt. of salicylic acid in dioctyl adipate.
[c]2,2'-dimorpholinodiethyl ether (DABCO ® DMDEE Catalyst, Air Products).
[d]10% by wt. of dibutyltin dilaurate in diisodecyl phthalate.
[e]BYK-088 (BYK-Chemie/ALTANA).

The coatings thus obtained were tested for tack-free time, for mechanical properties after curing and for bubble formation as described in example 6. In addition, odour formation was assessed qualitatively by smelling with the nose at a distance of 10 cm from a cured film.

The results of these tests are listed in table 6.

TABLE 6

Properties of the two-component coatings.

| Example | 15 | 16 |
|---|---|---|
| Tack-free time (min)[a] | 110 | 185 |
| Shore D after 28 days | 65 | 50 |
| Tensile strength (MPa) | 9.3 | 8.3 |
| Elongation at break (%) | 190 | 310 |
| Modulus of elasticity (MPa)[b] | 115 | 46 |
| Bubble formation | none | none |
| Odour formation | none | none |

[a] tack-free time in minutes.
[b] at 0.5-5.0% elongation.

The invention claimed is:

1. Aldimine of the formula (I)

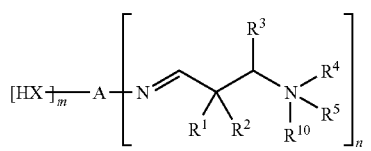

where
A is either
the radical of an amine after removal of n primary aliphatic amino groups and m HX groups
or
together with $R^7$ is an (n+2)-valent hydrocarbon radical which has 3 to 20 carbon atoms and optionally contains at least one heteroatom;
n is 1 or 2 or 3 or 4;
m is 0 or 1 or 2 or 3 or 4;
$R^1$ and $R^2$ are either
each independently a monovalent hydrocarbon radical having 1 to 12 carbon atoms
or
together are a divalent hydrocarbon radical having 4 to 12 carbon atoms which is part of an optionally substituted carbocyclic ring having 5 to 8 carbon atoms;
$R^3$ is a hydrogen atom or an alkyl group or an arylalkyl group or an alkoxycarbonyl group;
$R^4$ and $R^5$ are either
each independently a methyl group or a monovalent aliphatic, cycloaliphatic or arylaliphatic radical which has 2 to 12 carbon atoms and optionally has hydroxyl groups and optionally contains heteroatoms in the form of ether oxygen or tertiary amine nitrogen, with the proviso that $R^4$ has at least one hydroxyl group,
or
together are a divalent aliphatic radical which has at least one hydroxyl group and 4 to 12 carbon atoms, and is part of an optionally substituted heterocyclic ring having 5 to 8 ring atoms, this ring optionally containing further heteroatoms in the form of ether oxygen or tertiary amine nitrogen;
X is O or S or N—$R^6$ or N—$R^7$,
where $R^6$ is
either a monovalent hydrocarbon radical which has 1 to 20 carbon atoms and optionally has at least one carboxylic ester, nitrite, nitro, phosphonic ester, sulphone or sulphonic ester group,
or
a substituent of the formula (II)

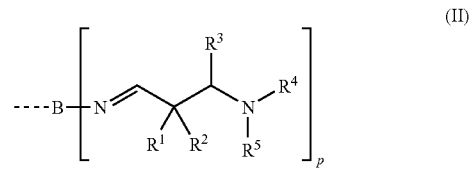

where
p is 0 or an integer from 1 to 10 000, and
B is a (p+1)-valent hydrocarbon radical which optionally contains ether oxygen, tertiary amine nitrogen, hydroxyl groups, secondary amino groups or mercapto groups; and
$R^7$ together with A is an (n+2)-valent hydrocarbon radical which has 3 to 20 carbon atoms and optionally contains at least one heteroatom.

2. Aldimine according to claim 1, wherein $R^1$ and $R^2$ are each a methyl group.

3. Aldimine according to claim 1, wherein $R^3$ is a hydrogen atom.

4. Aldimine according to claim 1, wherein $R^4$ and $R^5$ are each a 2-hydroxyethyl group or are each a 2-hydroxypropyl group.

5. Aldimine according to claim 1, wherein A is the radical of an amine B1 selected from the group consisting of N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethylpiperidine, 3-(4-aminobutyl)piperidine, diethylenetriamine (DETA), dipropylenetriamine (DPTA), bishexamethylenetriamine (BHMT), fatty diamines such as N-cocoalkyl-1,3-propanediamine, N-oleyl-1,3-propanediamine, N-soyaalkyl-1,3-propanediamine and N-tallowalkyl-1,3-propanediamine, 5-amino-1-pentanol, 6-amino-1-hexanol, 4-(2-amino-ethyl)-2-hydroxyethylbenzene, 3-aminomethyl-3,5,5-trimethylcyclohexanol, 2-(2-aminoethoxy)ethanol, triethylene glycol monoamine, 3-(2-hydroxyethoxy)propylamine, 3-(2-(2-hydroxyethoxy)ethoxy)propylamine and 3-(6-hydroxyhexyloxy)propylamine.

6. Aldimine according to claim 1, wherein A is the radical of an amine B2 selected from the group consisting of 1,6-hexamethylenediamine, 1,5-diamino-2-methylpentane (MPMD), 1,3-pentanediamine (DAMP), 1-amino-3-aminomethyl-3,5,5-trimethylcyclohexane (=isophoronediamine or IPDA), 2,2,4- and 2,4,4-trimethylhexamethylenediamine (TMD), 1,3-xylylenediamine, 1,3-bis(aminomethyl)cyclohexane, bis(4-aminocyclohexyl)methane, bis(4-amino-3-methylcyclohexyl)methane, 3(4),8(9)-bis(aminomethyl)-tricyclo[5.2.1.0$^{2,6}$]decane, 1,2-, 1,3- and 1,4-diaminocyclohexane, 1,4-diamino-2,2,6-trimethylcyclohexane, 3,6-dioxaoctane-1,8-diamine, 4,7-dioxadecane-1,10-diamine, 4-aminomethyl-1,8-octanediamine and polyoxyalkylenepolyamines having two or three amino groups.

7. Aldimine according to claim 1, wherein the aldimine has the formula (I')

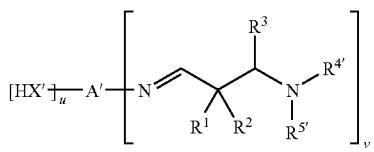

(I')

where
A' is either
  the radical of an amine after removal of v primary aliphatic amino groups and u HX' groups,
or
  together with $R^{7'}$ is a (v+2)-valent hydrocarbon radical which has 3 to 20 carbon atoms and optionally contains at least one heteroatom;
u is 1 or 2 or 3 or 4, and
v is 0 or 1 or 2 or 3 or 4,
with the proviso that u+v is 2 or 3 or 4 or 5;
$R^{4'}$ and $R^{5'}$ are either
  each independently a methyl group or a monovalent aliphatic, cycloaliphatic or arylaliphatic radical which has 2 to 12 carbon atoms and optionally has hydroxyl groups and optionally contains heteroatoms in the form of ether oxygen or tertiary amine nitrogen, with the proviso that $R^{4'}$ has at least one hydroxyl group, and that $R^{4'}$ and $R^5$ together have at least two hydroxyl groups,
or
  together are a divalent aliphatic radical which has at least two hydroxyl groups and 4 to 12 carbon atoms, and is part of an optionally substituted heterocyclic ring having 5 to 8 ring atoms, this ring optionally containing further heteroatoms in the form of ether oxygen or tertiary amine nitrogen;
X' is O or S or N—$R^{6'}$ or N—$R^{7'}$,
where $R^{6'}$ is
  either a monovalent hydrocarbon radical which has 1 to 20 carbon atoms and optionally has at least one carboxylic ester, nitrite, nitro, phosphonic ester, sulphone or sulphonic ester group,
or
  a substituent of the formula (II')

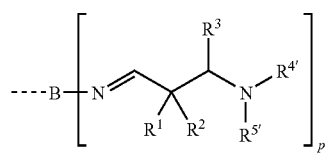

(II')

and
$R^7$ together with A' is a (v+2)-valent hydrocarbon radical which has 3 to 20 carbon atoms and optionally contains at least one heteroatom.

8. Aldimine according to claim 7, wherein (u+v) is 2 or 3.

9. Aldimine according to claim 7, wherein
either
  $R^{4'}$ has two hydroxyl groups and $R^{5'}$ has no hydroxyl group;
or
  $R^{4'}$ has one hydroxyl group and $R^{5'}$ has one hydroxyl group.

10. Aldimine according to claim 7, wherein the aldimine has the formula (I a)

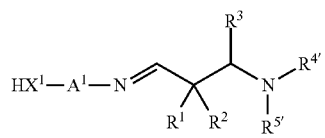

(I a)

where
$A^1$ has no active hydrogen and no primary amino groups and
is either
  a divalent hydrocarbon radical which has 2 to 20 carbon atoms and optionally contains at least one heteroatom,
or
  together with $R^9$ is a trivalent hydrocarbon radical which has 3 to 20 carbon atoms and optionally contains at least one heteroatom,
$X^1$ is O or S or N—$R^8$ or N—$R^9$,
  where $R^8$ is
    either a monovalent hydrocarbon radical which has 1 to 20 carbon atoms and optionally has at least one carboxylic ester, nitrite, nitro, phosphonic ester, sulphone or sulphonic ester group,
  or
    a substituent of the formula (II a)

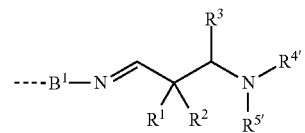

(II a)

where $B^1$ is a divalent hydrocarbon radical which has 2 to 12 carbon atoms and optionally has ether oxygen or tertiary amine nitrogen; and
$R^9$ together with $A^1$ is a trivalent hydrocarbon radical which has 3 to 20 carbon atoms and optionally contains at least one heteroatom.

11. Aldimine according to claim 7, wherein the aldimine has the formula (I b)

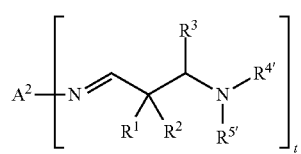

(I b)

where t is 2 or 3; and
$A^2$ is the radical of a polyamine with t primary amino groups after removal of t primary amino groups and contains no active hydrogen.

12. Process for preparing an aldimine according to claim 1, which comprises reaction of at least one amine B of the formula (III) with at least one sterically hindered, aliphatic aldehyde ALD which has at least one hydroxyl group and is of the formula (IV),

 (III)

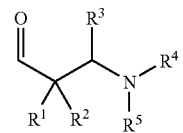 (IV)

where $X^a$ is O or S or N—$R^{6a}$ or N—$R^7$, where $R^{6a}$ is either a monovalent hydrocarbon radical which has 1 to 20 carbon atoms and optionally has at least one carboxylic ester, nitrile, nitro, phosphonic ester, sulphone or sulphonic ester group, or is a substituent of the formula (III')

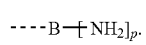 (III')

13. Process according to claim 12, wherein an aldehyde Y1 of the formula (V), an aldehyde Y2 of the formula (VI) and a secondary aliphatic amine C which has at least one hydroxyl group and is of the formula (VII) are converted with elimination of water to the aldehyde ALD of the formula (IV)

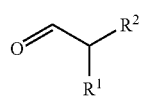 (V)

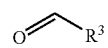 (VI)

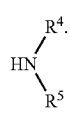 (VII)

14. Process according to claim 13, wherein the amine C which has at least one hydroxyl group and is of the formula (VII) is a secondary aliphatic amine which has at least two hydroxyl groups, and which is especially selected from the group consisting of diethanolamine, dipropanolamine, diisopropanolamine, 3-(2-hydroxyethylamino)-1-propanol and 3-(2-hydroxypropyl amino)-1-propanol, N-methyl-2,3-dihydroxypropylamine, 3,4-dihydroxypyrrolidine, 2,5-bis(hydroxymethyl)-pyrrolidine, 2,6-bis(hydroxymethyl)piperidine, 3,4- or 3,5-dihydroxypiperidine, dihydroxypropyl)pyrrolidine and 2-(2,3-dihydroxypropyl)-piperidine, and the reaction products of ammonia with two molecules which each have an epoxy group.

15. Aldimine of the formula (IX)

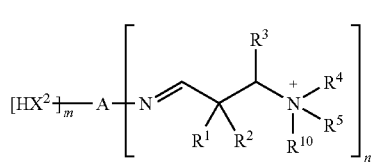 (IX)

where $R^{10}$ is a hydrogen atom or an alkyl, cycloalkyl or arylalkyl radical having 1 to 20 carbon atoms;

and $X^2$ is O or S or N—$R^{11}$ or N—$R^7$; where
$R^{11}$ is either a monovalent hydrocarbon radical which has 1 to 20 carbon atoms and optionally has at least one carboxylic ester, nitrite, nitro, phosphonic ester, sulphone or sulphonic ester group,
or is a substituent of the formula (IX')

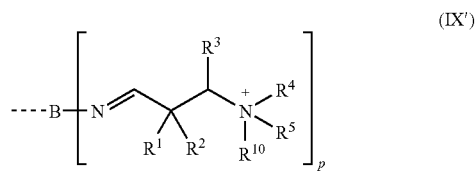 (IX')

which is obtained by protonating or alkylating an aldimine of the formula (I) according to claim 1.

16. A method of preparing a composition based on isocyanates or epoxy resins, comprising providing an aldimine of the formula (I) according to claim 1 or an aldimine of the formula (IX)

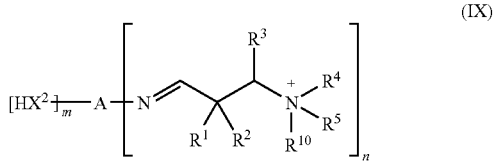 (IX)

where $R^{10}$ is a hydrogen atom or an alkyl, cycloalkyl or arylalkyl radical having 1 to 20 carbon atoms;
and $X^2$ is O or S or N—$R^{11}$ or N—$R^7$; where
$R^{11}$ is either a monovalent hydrocarbon radical which has 1 to 20 carbon atoms and optionally has at least one carboxylic ester, nitrite, nitro, phosphonic ester, sulphone or sulphonic ester group,
or is a substituent of the formula (IX')

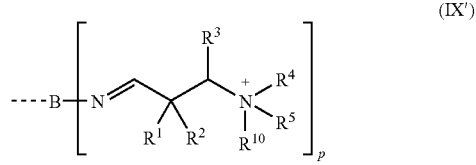 (IX')

which is obtained by protonating or alkylating an aldimine of the formula (I) according to claim 1.

17. Curable composition comprising at least one polyisocyanate and at least one aldimine of the formula (I) according to claim 1 or an aldimine of the formula (IX)

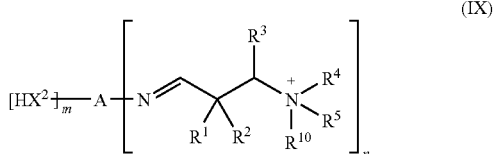 (IX)

where $R^{10}$ is a hydrogen atom or an alkyl, cycloalkyl or arylalkyl radical having 1 to 20 carbon atoms;

and $X^2$ is O or S or N—$R^{11}$ or N—$R^7$; where
$R^{11}$ is either a monovalent hydrocarbon radical which has 1 to 20 carbon atoms and optionally has at least one carboxylic ester, nitrite, nitro, phosphonic ester, sulphone or sulphonic ester group,
or is a substituent of the formula (IX')

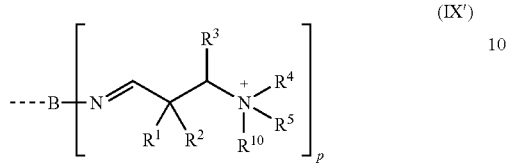

which is obtained by protonating or alkylating an aldimine of the formula (I) according to claim 1.

18. Curable composition comprising at least one polyisocyanate and at least one aldimine of the formula (I') according to claim 7.

19. Curable composition according to claim 18, wherein it is a one-component composition, and in that it comprises at least one polyisocyanate whose isocyanate groups are present in the form of blocked isocyanate groups.

20. Curable composition according to claim 18, wherein it is a two-component composition consisting of a component K1 and a component K2, which component K1 comprises at least one polyisocyanate P.

21. Curable composition according to claim 20, wherein the polyisocyanate P is a polyisocyanate PI in the form of a monomeric di- or triisocyanate or of an oligomer of a monomeric diisocyanate or of a derivative of a monomeric diisocyanate, especially of 1,6-hexamethylene diisocyanate (HDI), 1-isocyanato-3,3,5-trimethyl-5-isocyanato-methyl-cyclohexane (=isophorone diisocyanate or IPDI), 2,4- and 2,6-tolylene diisocyanate and any mixtures of these isomers (TDI), or 4,4'-, 2,4'- and 2,2'-diphenylmethane diisocyanate and any mixtures of these isomers (MDI).

22. Curable composition according to claim 20, wherein the polyisocyanate P is a polyurethane polymer PUP which has isocyanate groups.

23. Curable composition according to claim 20, wherein component K2 comprises water.

24. Cured composition obtained by the reaction of a curable composition according to claim 17 and water.

25. Process for bonding a substrate S1 to a substrate S2, which comprises the steps of
i) applying a curable composition according to claim 17 to a substrate S1;
ii) contacting the applied composition with a substrate S2 within the open time of the composition;
or
i') applying a composition according to claim 17 to a substrate S1 and to a substrate S2;
ii') contacting the applied compositions with one another within the open time of the composition;
the substrate S2 consisting of the same material as, or a different material than, the substrate S1.

26. Process for sealing, which comprises the step of
i') applying a curable composition according to claim 17 between a substrate S1 and a substrate S2, such that the composition is in contact with the substrate S1 and the substrate S2;
the substrate S2 consisting of the same material as, or a different material than, the substrate S1.

27. Process for coating a substrate S1, which comprises the step of
i''') applying a curable composition according to claim 17 to a substrate S1 within the open time of the composition.

28. Process according to claim 25, wherein the substrate S1 and/or the substrate S2 is an inorganic substrate; natural stone; a metal; an alloy; an organic substrate; a plastic; a coated substrate; a paint; or a coating.

29. Article which has been bonded, sealed or coated by a process according to claim 25.

30. Article according to claim 29, wherein the article is a built structure; an industrial good; a consumer good; a domestic appliance; a mode of transport; an installable component on a mode of transport; or an article in the furniture, textile, or packaging industry.

* * * * *

UNITED STATES PATENT AND TRADEMARK OFFICE
CERTIFICATE OF CORRECTION

PATENT NO. : 8,455,100 B2  Page 1 of 1
APPLICATION NO. : 12/669717
DATED : June 4, 2013
INVENTOR(S) : Burckhardt It is certified that error appears in the above-identified patent and that said Letters Patent is hereby corrected as shown below:

In the Claims

In Col. 39, Line 19-27, Formula (I) in Claim 1 should be shown as:

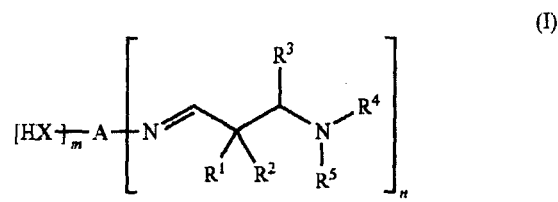

(I)

Signed and Sealed this
Twenty-ninth Day of October, 2013

Teresa Stanek Rea
*Deputy Director of the United States Patent and Trademark Office*